US010086201B2

(12) United States Patent
Chang et al.

(10) Patent No.: US 10,086,201 B2
(45) Date of Patent: *Oct. 2, 2018

(54) ELECTRONIC STIMULATION DEVICE, METHOD OF TREATMENT AND ELECTRONIC STIMULATION SYSTEM

(71) Applicant: GiMer Medical Co., Ltd., New Taipei (TW)

(72) Inventors: Chi-Heng Chang, New Taipei (TW); Wei-Tso Lin, New Taipei (TW); Chan-Yi Cheng, New Taipei (TW); Chii-Wann Lin, New Taipei (TW); Yeong-Ray Wen, New Taipei (TW)

(73) Assignee: GIMER MEDICAL CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/925,379

(22) Filed: Oct. 28, 2015

(65) Prior Publication Data

US 2016/0045735 A1  Feb. 18, 2016

Related U.S. Application Data

(63) Continuation-in-part of application No. 14/049,235, filed on Oct. 9, 2013, now Pat. No. 9,526,889.

(51) Int. Cl.
*A61N 1/05* (2006.01)
*A61N 1/36* (2006.01)
*A61N 1/06* (2006.01)

(52) U.S. Cl.
CPC ....... *A61N 1/36071* (2013.01); *A61N 1/0551* (2013.01); *A61N 1/0556* (2013.01);
(Continued)

(58) Field of Classification Search
CPC .............. A61N 1/36071; A61N 1/0551; A61N 1/0556; A61N 1/06; A61N 1/36171
See application file for complete search history.

(56) References Cited

U.S. PATENT DOCUMENTS

| 4,398,537 A | 8/1983 | Holmbo |
| 7,330,762 B2 | 2/2008 | Boveja et al. |

(Continued)

FOREIGN PATENT DOCUMENTS

| CN | 1138829 A | 12/1996 |
| CN | 101610810 A | 12/2009 |

(Continued)

OTHER PUBLICATIONS

Lin et al., "The effect of high and low frequency electroacupuncture in pain after lower abdominal surgery," Pain, 99 (2002), pp. 509-514.

(Continued)

*Primary Examiner* — Amanda Hulbert
*Assistant Examiner* — Natasha Patel
(74) *Attorney, Agent, or Firm* — Muncy, Geissler, Olds & Lowe, P.C.

(57) ABSTRACT

An electronic stimulation device is adapted for electrically stimulating a target zone of an organism with relative low pain sensations without generating relative much sensations of paresthesia. The electronic stimulation device comprises at least one electronic stimulation unit. The electronic stimulation unit includes at least one first electrode and at least one second electrode. The electronic stimulation unit receives a high-frequency electrical stimulation signal to impel the first electrode and the second electrode to generate an electric field. The range of the electric field covers the target zone, and the electric field strength ranges from 100 V/m to 1000 V/m. The frequency of the high-frequency (Continued)

electrical stimulation signal ranges from 200 KHz to 1000 KHz.

23 Claims, 24 Drawing Sheets

(52) U.S. Cl.
CPC ........... *A61N 1/06* (2013.01); *A61N 1/36153* (2013.01); *A61N 1/36171* (2013.01)

(56) References Cited

U.S. PATENT DOCUMENTS

| | | | |
|---|---|---|---|
| 7,337,006 | B2 | 2/2008 | Kim et al. |
| 7,447,546 | B2 | 11/2008 | Kim et al. |
| 7,450,993 | B2 | 11/2008 | Kim et al. |
| 7,502,651 | B2 | 3/2009 | Kim et al. |
| 7,580,753 | B2 | 8/2009 | Kim et al. |
| 8,082,039 | B2 | 12/2011 | Kim et al. |
| 8,170,675 | B2 | 5/2012 | Alataris et al. |
| 8,209,021 | B2 | 6/2012 | Alataris et al. |
| 8,229,565 | B2 | 7/2012 | Kim et al. |
| 8,249,701 | B2 | 8/2012 | Imran et al. |
| 8,255,057 | B2 | 8/2012 | Fang et al. |
| 8,311,639 | B2 | 11/2012 | Parker et al. |
| 8,355,792 | B2 | 1/2013 | Alataris et al. |
| 8,355,797 | B2 | 1/2013 | Caparso et al. |
| 8,359,102 | B2 | 1/2013 | Alataris et al. |
| 8,359,103 | B2 | 1/2013 | Alataris et al. |
| 8,380,318 | B2 | 2/2013 | Kishawi et al. |
| 8,396,559 | B2 | 3/2013 | Alataris et al. |
| 8,423,147 | B2 | 4/2013 | Alataris et al. |
| 8,428,748 | B2 | 4/2013 | Alataris et al. |
| 8,457,759 | B2 | 6/2013 | Parker et al. |
| 8,498,710 | B2 | 7/2013 | Walker et al. |
| 8,509,905 | B2 | 8/2013 | Alataris et al. |
| 8,509,906 | B2 | 8/2013 | Walker et al. |
| 8,768,472 | B2 | 7/2014 | Fang et al. |
| 8,961,385 | B2 * | 2/2015 | Pilla .................. A61N 1/40 600/14 |
| 2004/0162590 | A1* | 8/2004 | Whitehurst ........ A61N 1/36071 607/17 |
| 2005/0154425 | A1 | 7/2005 | Boveja et al. |
| 2006/0116721 | A1 | 6/2006 | Yun et al. |
| 2006/0149337 | A1 | 7/2006 | John |
| 2007/0021803 | A1* | 1/2007 | Deem ................. A61N 1/0412 607/46 |
| 2009/0062886 | A1 | 3/2009 | O'Handley et al. |
| 2009/0093858 | A1* | 4/2009 | DiUbaldi ............ A61N 1/0514 607/17 |
| 2009/0270943 | A1 | 10/2009 | Maschino |
| 2010/0152811 | A1 | 6/2010 | Flaherty |
| 2011/0130804 | A1 | 6/2011 | Lin et al. |
| 2011/0137381 | A1* | 6/2011 | Lee ..................... A61N 1/0529 607/62 |
| 2012/0029591 | A1* | 2/2012 | Simon ................. A61N 1/40 607/42 |
| 2012/0035687 | A1* | 2/2012 | Lu ..................... A61N 1/36125 607/61 |
| 2012/0296389 | A1 | 11/2012 | Fang et al. |
| 2013/0079862 | A1 | 3/2013 | Ellrich |
| 2013/0096643 | A1 | 4/2013 | Fang et al. |
| 2013/0116752 | A1 | 5/2013 | Parker et al. |
| 2013/0138178 | A1 | 5/2013 | Lin et al. |
| 2013/0144359 | A1 | 6/2013 | Kishawi et al. |
| 2013/0317564 | A1 | 11/2013 | Lin et al. |
| 2014/0039579 | A1 | 2/2014 | Mashiach et al. |
| 2014/0257437 | A1 | 9/2014 | Simon et al. |
| 2015/0100112 | A1 | 4/2015 | Chang et al. |

FOREIGN PATENT DOCUMENTS

| | | |
|---|---|---|
| CN | 102120060 A | 7/2011 |
| CN | 102939066 A | 2/2013 |
| WO | WO 95/19804 | 7/1995 |
| WO | WO 2008/094345 A1 | 12/1996 |

OTHER PUBLICATIONS

Wen et al., "A minimal stress model for the assessment of electroacupuncture analgesia in rats under halothane," European Journal of Pain, 11 (2007), pp. 733-742.

Zhuang et al., "Role of the CX3CR1/p38 MAPK pathway in spinal microglia for the development of neuropathic pain following nerve injury-induced cleavage of fractalkine," Brain Behav Immun., 21(5), Jul. 2007, pp. 642-651.

Wen et al., "Nerve conduction blockade in the sciatic nerve prevents but does not reverse the activation of p38 mitogen-activated protein kinase in spinal microglia in the rat spared nerve injury model," Anesthesiology, 107 (2007), pp. 312-321.

Shieh et al., "A novel fuzzy pain demand index derived from patient-controlled analgesia for postoperative pain," IEEE Transactions on Biomedical Engineering, vol. 54, No. 12, Dec. 2007, pp. 2123-2132.

Shieh et al., Fuzzy Logic: Theory, Programming and Applications, 1$^{st}$ edition, Chapter 7, "Fuzzy logic applied in multidimensional model of postoperative pain derived from patient-controlled analgesia," published by Nova Science Publishers, Jun. 2009, pp. 247-267.

Chiu et al., "Pain control on demand based on pulsed radio-frequency stimulation of the dorsal root ganglion using a batteryless implantable CMOS SoC," IEEE Transactions on Biomedical Circuits and Systems, vol. 4, No. 6, Dec. 2010, pp. 350-359.

Lin et al., IEEE International Solid State Circuits Conference, "ISSCC 2010/Session 12/Emerging Medical Applications/12.1," Feb. 7-11, 2010, pp. 234-236.

Wen et al., "DNIC-mediated analgesia produced by a supramaximal electrical or a high-dose formalin conditioning stimulus: roles of opioid and α2-adrenergic receptors," Journal of Biomedical Science, 17:19, 2010, pp. 1-13.

Yeh et al., "A novel continuous visual analog scale model derived from pain-relief demand index via Hilbert Huang transform for postoperative pain," Journal of Medical and Biological Engineering, 31(3), Jan. 2011, pp. 169-176.

Chang et al., "Feasibility Study of Implantable Pulsed-Radiofrequency Stimulator with Verification on Sciatica Rat Model," Institute of Biomedical Engineering National Taiwan University, 2009, 2 pages.

* cited by examiner

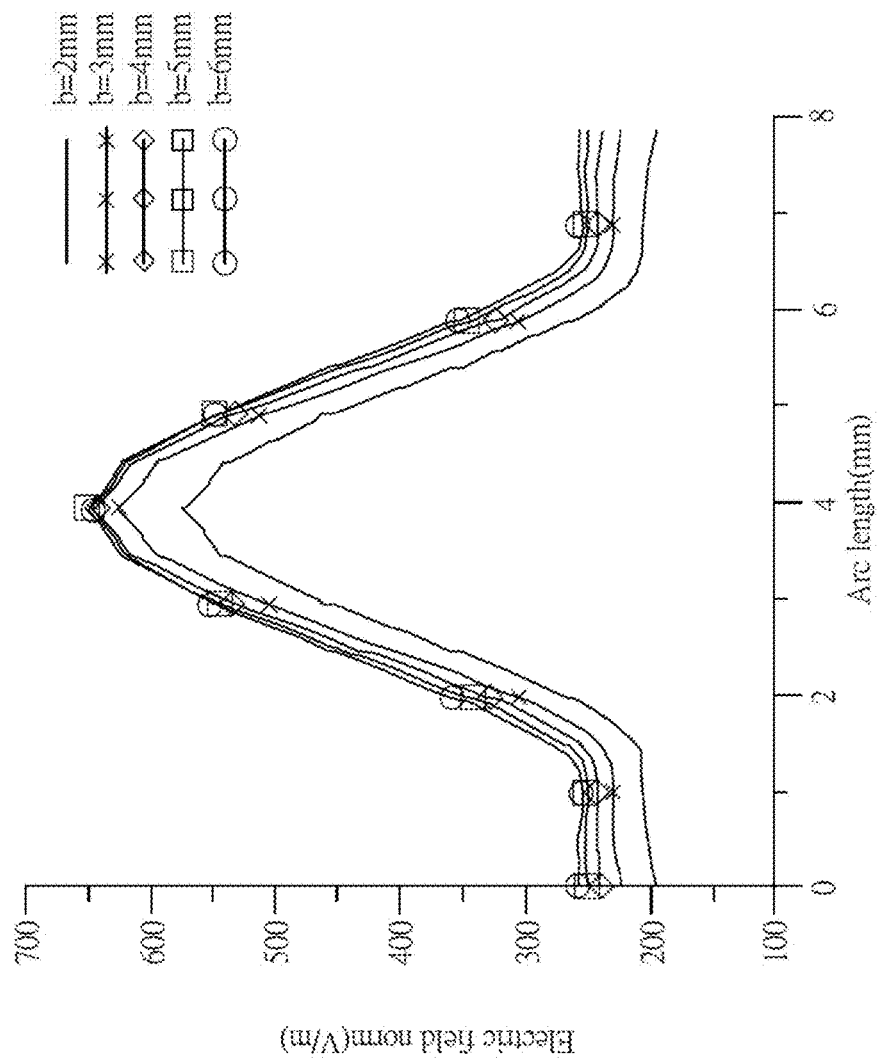

ELECTRONIC STIMULATION DEVICE, METHOD OF TREATMENT AND ELECTRONIC STIMULATION SYSTEM

CROSS REFERENCE TO RELATED APPLICATIONS

This application is a Continuation-In-Part of U.S. application Ser. No. 14/049,235 filed on Oct. 9, 2013.

BACKGROUND

Technical Field

The invention relates to an electronic stimulation device, in particular to an electronic stimulation device for electrically stimulating a target zone of an organism with relative low pain sensations without generating relative much sensations of paresthesia.

Related Art

The human nerve system provides transmission paths for the commands issued from the brain. The human nerve has a threshold and the threshold is often reduced around a damaged spot of the nerve. Therefore, uncomfortable pain or ache is frequently and easily felt at this spot. After a period of time, this spot would become a source of chronic pain.

Clinically, an approach called Continuous Radiofrequency (CRF) or Radiofrequency Ablation is widely applied to ease various nerve pains. The approach inserts a pin into the proximity of related nerve tissue, applies continuous high-frequency signal to create high temperature so as to destroy the nerve tissue, thereby alleviating the nerve pain. However, due to the human body's self-repair function, the destroyed nerve tissue will try to heal itself When this happens, newly developed tissue grows randomly on the destroyed tissue, and it is quite common that a neuroma is formed. The neuroma, once formed, often oppresses the nerve system and causes even more serious pain.

SUMMARY

An electronic stimulation device is adapted for electrically stimulating a target zone of an organism with relative low pain sensations without generating relative much sensations of paresthesia. The electronic stimulation device comprises at least one electronic stimulation unit. The electronic stimulation unit includes at least one first electrode and at least one second electrode. The electronic stimulation unit receives a high-frequency electrical stimulation signal to impel the first electrode and the second electrode to generate an electric field. The range of the electric field covers the target zone, and the electric field strength ranges from 100 V/m to 1000 V/m. The frequency of the high-frequency electrical stimulation signal ranges from 200 KHz to 1000 KHz.

In one embodiment, the high-frequency electrical stimulation signal is a pulse signal and its pulse frequency ranges from 0 to 1 KHz.

In one embodiment, the frequency of the high-frequency electrical stimulation signal ranges from 200 KHz to 450 KHz or ranges from 550 KHz to 1000 KHz.

In one embodiment, the voltage of the high-frequency electrical stimulation signal ranges from −10V to −1V or ranges from 1V to 10V.

In one embodiment, the current of the high-frequency electrical stimulation signal ranges from 2 mA to 50 mA.

In one embodiment, the distance from the first electrode to the second electrode ranges from 1 mm to 7 mm, and the distance between the first electrode, the second electrode and the target zone ranges from 0 to 10 mm.

In one embodiment, the high-frequency electrical stimulation signal is adapted to block the neurotransmission in the target zone.

In one embodiment, the target zone is brain, vertebral column, dorsal root ganglion and/or spinal dorsal horn.

In one embodiment, the electronic stimulation unit receives a low-frequency electrical stimulation signal, and the frequency of the low-frequency electrical stimulation signal is less than 1 KHz.

A method of treatment is applied to electrically stimulate a target zone of an organism by a stimulation device with relative low pain sensations without generating relative much sensations of paresthesia. The stimulation device includes an electronic stimulation unit including at least one first electrode and at least one second electrode. The method comprises: placing the electronic stimulation unit near the target zone; delivering a high-frequency electrical stimulation signal by the electronic stimulation unit; generating an electric field covering the target zone by the first electrode and the second electrode, wherein the electric field strength ranges from 100 V/m to 1000 V/m; and electrically stimulating the target zone. The frequency of the high-frequency electrical stimulation signal ranges from 200 KHz to 1000 KHz.

In one embodiment, the high-frequency electrical stimulation signal is a pulse signal and its pulse frequency ranges from 0 to 1 KHz.

In one embodiment, the frequency of the high-frequency electrical stimulation signal ranges from 200 KHz to 450 KHz or ranges from 550 KHz to 1000

In one embodiment, the voltage of the high-frequency electrical stimulation signal ranges from −10V to −1V or ranges from 1V to 10V.

In one embodiment, the current of the high-frequency electrical stimulation signal ranges from 2 mA to 50 mA.

In one embodiment, the high-frequency electrical stimulation signal is used by the electronic stimulation device to block the neurotransmission in the target zone.

In one embodiment, the target zone is brain, vertebral column, dorsal root ganglion and/or spinal dorsal horn.

An electronic stimulation system comprises a control unit and an electronic stimulation device. The electronic stimulation device comprises at least one electronic stimulation unit including at least one first electrode and at least one second electrode. The controller directs the electronic stimulation unit to deliver a high-frequency electrical stimulation signal to impel the first electrode and the second electrode to generate an electric field. The range of the electric field covers the target zone and the electric field strength ranges from 100 V/m to 1000 V/m for electrically stimulating the target zone. The frequency of the high-frequency electrical stimulation signal ranges from 200 KHz to 1000 KHz.

In one embodiment, the frequency of the high-frequency electrical stimulation signal ranges from 200 KHz to 450 KHz or ranges from 550 KHz to 1000 KHz.

In one embodiment, the voltage of the high-frequency electrical stimulation signal ranges from −10V to −1V or ranges from 1V to 10V.

In one embodiment, the current of the high-frequency electrical stimulation signal ranges from 2 mA to 50 mA.

BRIEF DESCRIPTION OF THE DRAWINGS

The embodiments will become more fully understood from the detailed description and accompanying drawings, which are given for illustration only, and thus are not limitative of the present invention, and wherein:

FIG. 5A and FIG. 5B are schematic diagrams of the electric field simulation at the condition that the electronic stimulation device operates at different electrode intervals and different frequencies of the electrical stimulation signals;

DETAILED DESCRIPTION OF THE INVENTION

The embodiments of the invention will be apparent from the following detailed description, which proceeds with reference to the accompanying drawings, wherein the same references relate to the same elements.

Figure 1A:
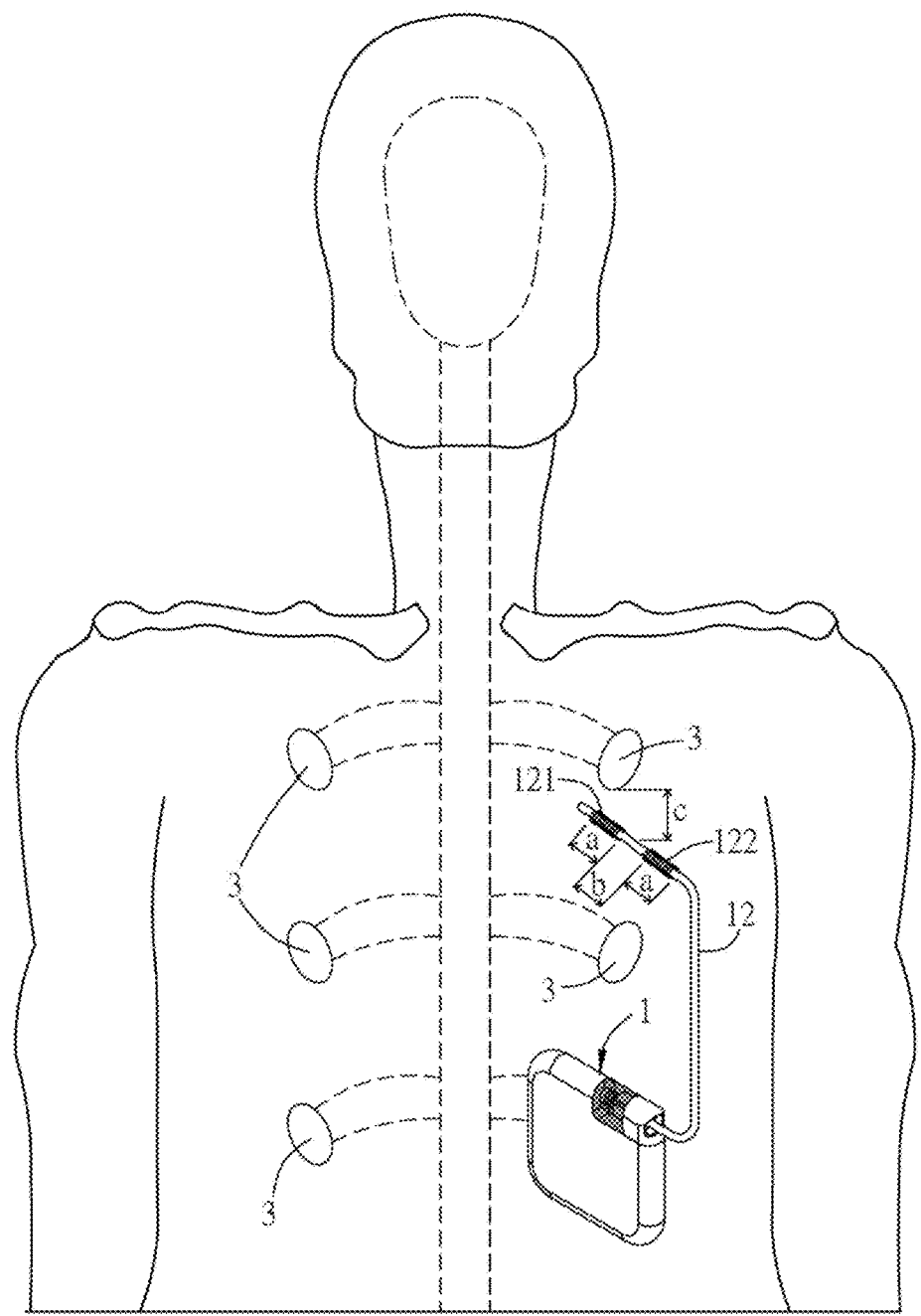
FIG. 1A is a schematic diagram showing the electronic stimulation device applied to the dorsal root ganglion according to the first embodiment.

FIG. 1A is a schematic diagram showing the electronic stimulation device applied to the dorsal root ganglion according to the first embodiment. Referring to FIG. 1A, an electronic stimulation device 1 is applied to electrically stimulate a target zone of an organism. In the embodiment, the target zone is dorsal root ganglion 3 for example. Alternatively, the target zone may be for example but not limited to brain, vertebral column, and/or spinal dorsal horn of an organism. The vertebral column may be T9 vertebrae or T10 vertebrae for example. The following paragraphs will describe the elements and applications of the electronic stimulation device 1.

For the sake of clarity regarding the step details of the method, the circuits and interaction of the electronic stimulation device 1 and the controller 2 are explained first in the following paragraphs. Then, the following paragraphs describe electrically stimulating the target zone of the organism by the electronic stimulation device 1 of the embodiment. However, the descriptions in the following embodiments are exemplary but not intended to limit the scope of the invention.

Figure 1B:
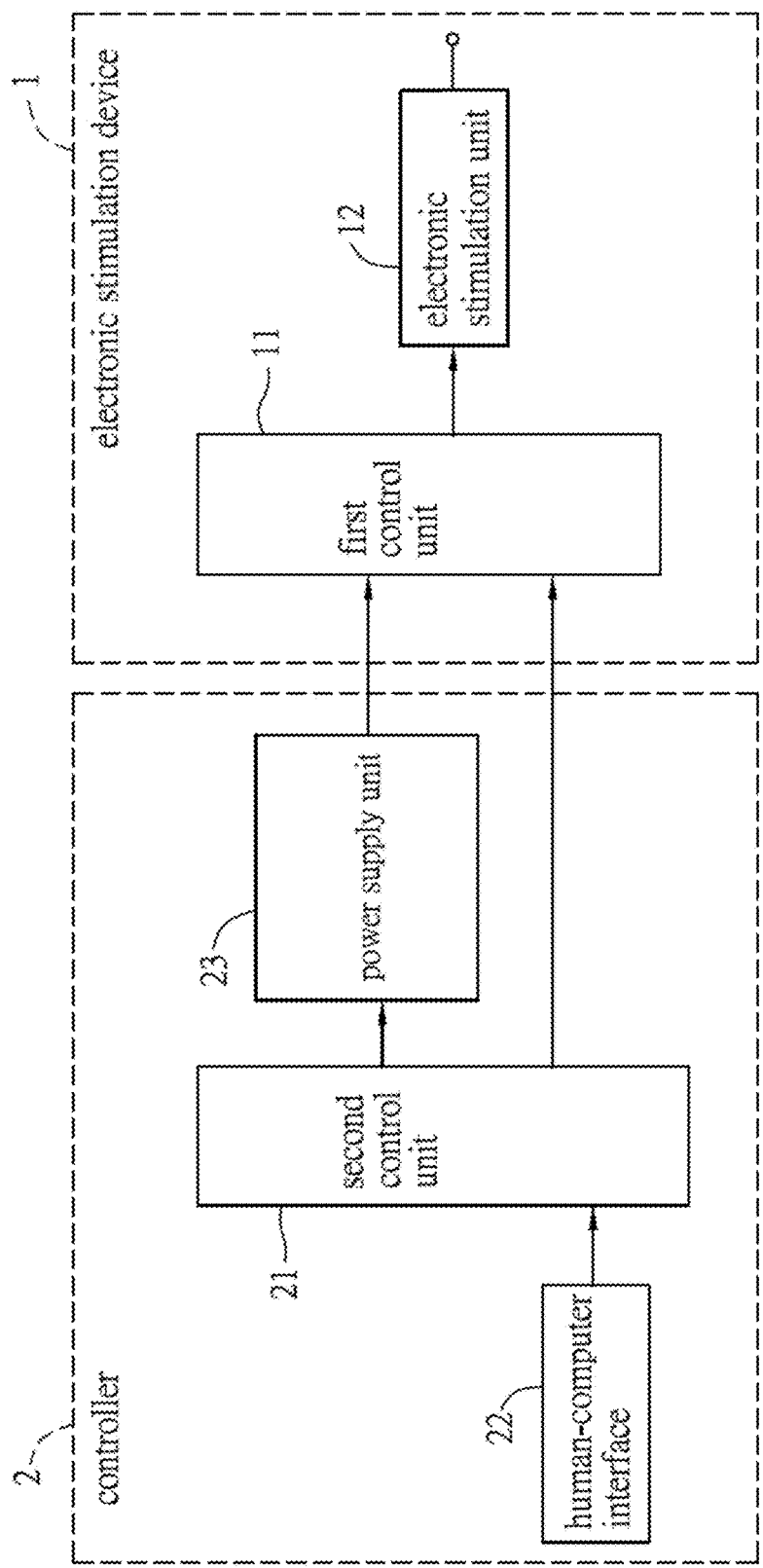
FIG. 1B is a circuit block diagram of the electronic stimulation device and the controller in FIG. 1A.

FIG. 1B is a circuit block diagram of the electronic stimulation device and the controller in FIG. 1A. Referring to FIG. 1B, a controller 2 provides configuration parameters and supplies energy for the electronic stimulation device 1. Because the controller 2 does not need to be implanted in the organism, it may be called the external controller 2. Elements of the electronic stimulation device 1 and the controller 2 and their relationships will be described in the following paragraphs.

In the embodiment, the electronic stimulation device 1 includes a first control unit 11 and an electronic stimulation unit 12. The electronic stimulation unit 12 is coupled to the first control unit 11. The controller 2 includes a second control unit 21, a human-computer interface 22 and a power supply unit 23. The human-computer interface 22 is coupled to the second control unit 21. The power supply unit 23 is also coupled to the second control unit 21 and acts as the power source of the controller 2. The power supply unit 23 may be a battery or a rechargeable battery, or it may be a power adapter connected to mains electricity to supply electrical power.

In the embodiment, the user may use the human-computer interface 22 to operate the controller 2. Before beginning, the system default values of the controller 2 is initialized. Then, he may also use the human-computer interface 22 to input the required configuration parameters to the second control unit 21. In the embodiment, the human-computer interface 22 may be for example but not limited to touch button, touch panel, physical button or their combination. The second control unit 21 instructs the power supply unit 23 to supply DC power to the elements of the electronic stimulation device 1 (for example the electronic stimulation unit 12) to operate.

The first control unit 11 and the second control unit 21 may be implemented with digital circuit such as IC or implemented with analog circuit. For example, IC may be a micro-processor, a MCU, a programmable logic gate array (for example FPGA or CPLD) or ASIC. In the embodiment, it is a MCU for example but not limited thereto.

In the embodiment, the electronic stimulation device 1 is an implantable electronic stimulation device for example. The implantable electronic stimulation device means that at least one portion of the element of the electronic stimulation device 1 is implanted in the individual body (for example: subcutaneous). Moreover, the electronic stimulation device 1 may be changed to a transcutaneous electronic stimulation device depending on the symptom and requirement of the patient. In the embodiment, the electronic stimulation unit 12 is adapted to be implanted in the individual. The first control unit 11 may be implanted within the individual or disposed outside the individual depending on actual or design requirement. If the electronic stimulation unit 12 is prepared to be implanted into one individual, it is better to implant the device in near the dorsal root ganglion of the spinal nerve relevant to the patient's pain. The individual preferably is an organism, and it may include mammals such as mouse, human, rabbit, cattle, sheep, pig, monkey, dog, cat, etc. Preferably, it is human. For example, it is human.

Figure 2A:
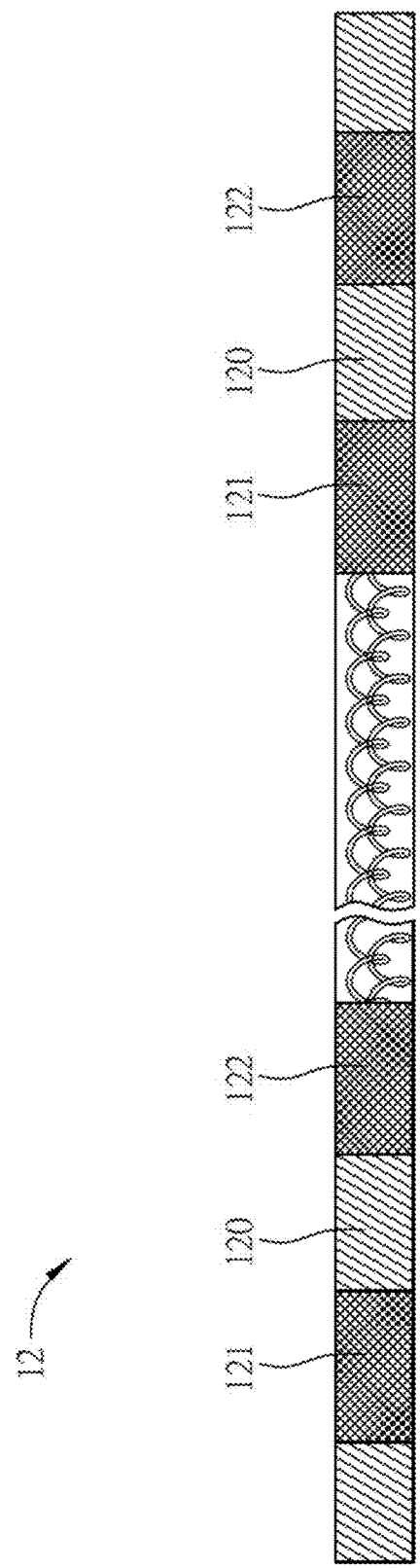
FIG. 2A and 2B are enlarged diagrams showing a portion of the electronic stimulation unit in FIG. 1.
Figure 2B:
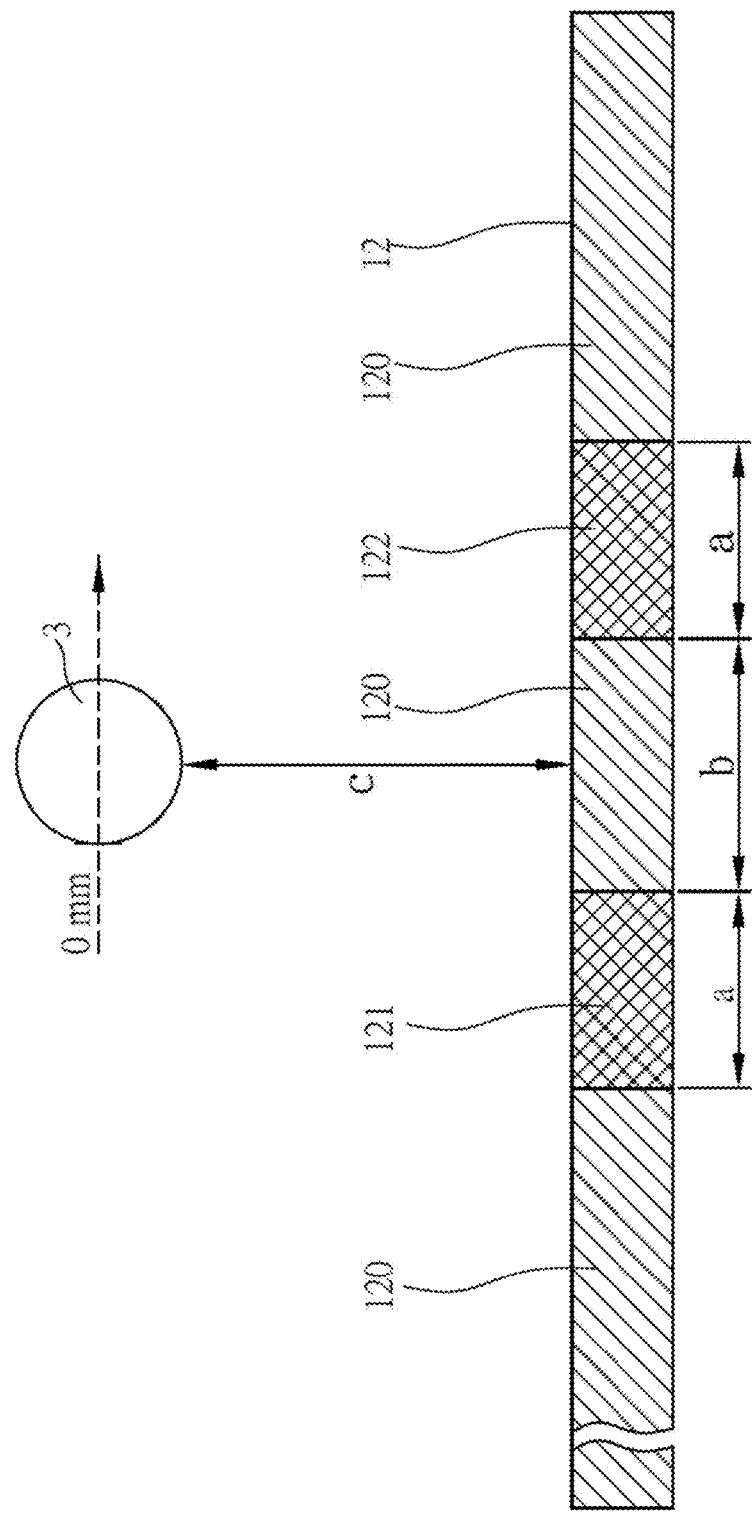

As to the configuration of the electronic stimulation unit 12, referring to FIG. 1A and FIG. 2B, the electronic stimulation unit 12 comprises a flexible transmission lead including at least one first electrode 121 and at least one second electrode 122. In the embodiment, it includes a pair of electrodes, namely a positive electrode 121 and a negative electrode 122 for example. In addition, there are maybe two pairs, three pairs or more than three pairs of electrodes of the electronic stimulation unit 12, and they may be evenly distributed on the transmission lead, namely the electronic stimulation unit 12. The above electrodes operate in bipolar mode to generate an electric field between the first electrode 121 and the second electrode 122. In the embodiment, between the first electrode 121 and the second electrode, there are coils or wires formed from winding coaxial conductor which are electrically connected to the electrodes. For example, the material of the first electrode 121 and the second electrode 122 may be metal for example platinum, silver, gold or other conductive metal. Between the first electrode 121 and the second electrode 122, a zone is defined by the coils or wires which are compactly wound cable electrically connected to the electrodes. The first electrode 121 and the second electrode 122 are disposed at one end of the electronic stimulation unit 12, two contacts 123 acting as the positive and negative electrodes are disposed at the other end of the electronic stimulation unit 12. The two contacts 123 are electrically connected or coupled to the first control unit 11. The first electrode 121 and the second electrode 122 are respectively linked to compactly wound coils, and they are linked to the contacts 123 through the wires. Besides, the wires of the electronic stimulation unit 12 beyond the first electrode 121 and the second electrode 122 is covered by an insulator 120. In FIG. 2A, the insulator 120 is removed to show the coil disposed between the electrodes in the electronic stimulation unit 12.

The range of the individual length a of each electrode depends on actual or design requirement. The electrode length a is between 0.5~6 mm, preferably between 1~4 mm. The individual length a of the first electrode 121 and the second electrode 122 means that the length of the electrode in the direction parallel to the extension direction of the major axis of the cable of the electronic stimulation unit 12 on the condition that it is not implanted and the electronic stimulation unit 12 is horizontally spread. The range of the individual length a of the first electrode 121 and the second electrode 122 depends on actual or design requirement. For example, the length a is between 1~3 mm. The distance b between the first electrode 121 and the second electrode 122 is between 1~7 mm, preferably between 1~4 mm. For example, the distance b of the two adjacent ends of the adjacent first and second electrodes 121,122 is preferably between 1~4 mm.

A second interval distance c exists between the first electrode 121 and the second electrode 122 of the electronic stimulation unit 1 and the dorsal root ganglion 3. The second interval distance c is defined as the shortest distance from the midpoint of the adjacent first and second electrodes 121, 122 to the dorsal root ganglion 3. In the embodiment, the second interval distance c ranges from 0 to 10 mm, preferably from 0 to 5 mm. If the distance c is 0, the midpoint of the first electrode 121 and the second electrode 122 in the projection direction overlaps the dorsal root ganglion 3.

Figure 1C:
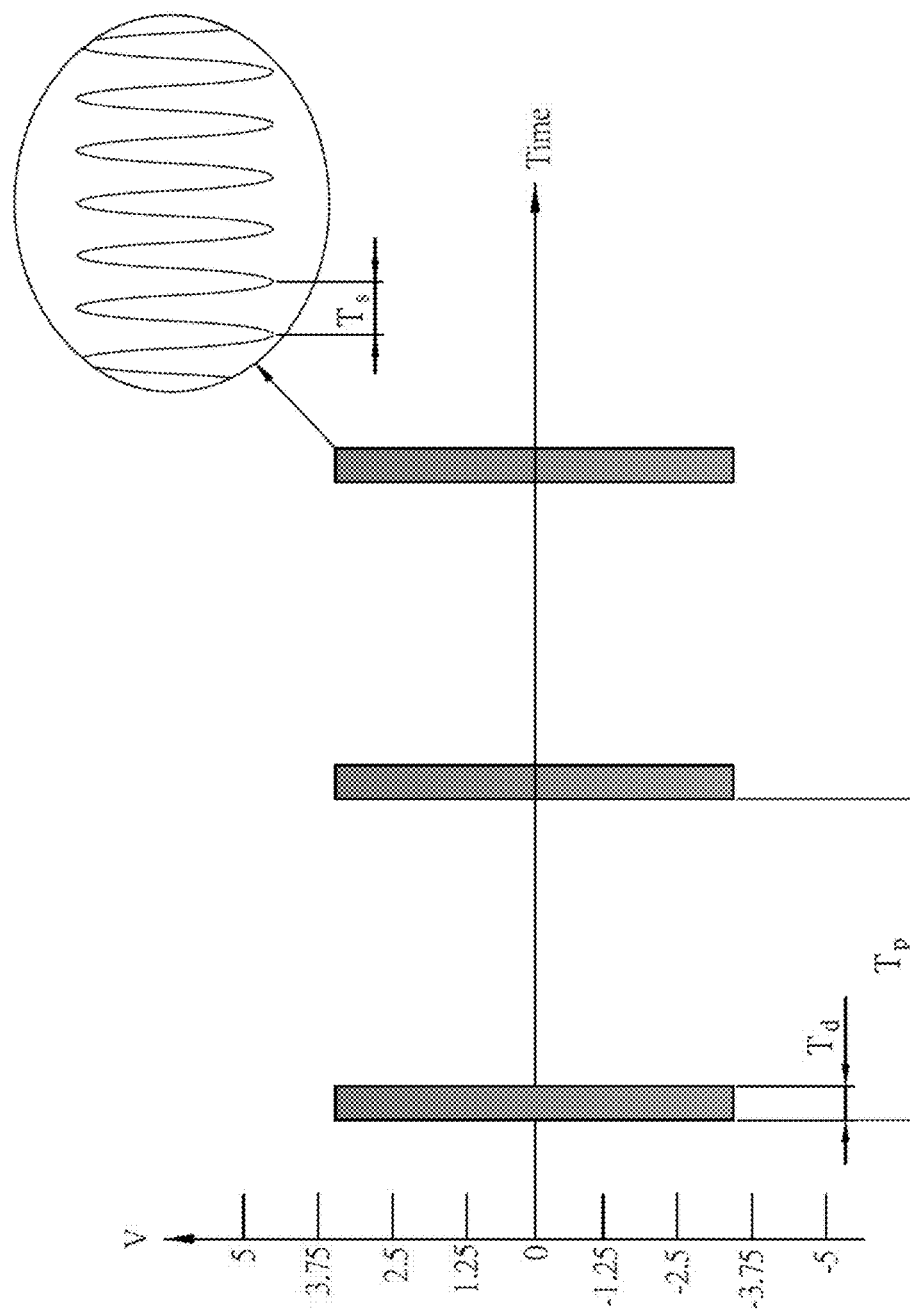
FIG. 1C is a schematic diagram showing the pulse signal of the electrical stimulation signal of the electronic stimulation device in FIG. 1.

Referring to FIG. 1C, in the embodiment, the electrical stimulation signal outputted from the electronic stimulation device 1 may be a continuous sine wave, a continuous triangle wave or an electrical stimulation signal of high-frequency pulse. If it is an electrical stimulation pulse signal, one pulse cycle time Tp has a plurality of pulse signals and at least one period of rest time. One pulse cycle time is the reciprocal of pulse repetition frequency. The pulse repetition frequency (also called pulse frequency) is between 0~1 KHz, preferably between 1~100 Hz. In the embodiment, the pulse repetition frequency of the electrical stimulation signal is about 2 Hz. Besides, the duration time Td of pulses in one pulse cycle time is between 1~250 ms, preferably between 10~100 ms. In the embodiment it is 25 ms for example.

Referring to FIG. 1C, in the embodiment, the electronic stimulation unit 12 is adapted to transmit a high-frequency electrical stimulation signal. For example, the patient (or healthcare workers) uses the controller 2 to set the electrical stimulation frequency, stimulation period, stimulation intensity and/or other parameters of the high-frequency electrical stimulation signal. Then, the controller 2 outputs the parameters and energy to the electronic stimulation device 1, and directs the electronic stimulation unit 1 to output signal via the first control unit 11. In the embodiment, the frequency of the high-frequency electrical stimulation signal is about 600 KHz. In other words, its stimulation cycle time Ts is about 1.67 μs.

For example, the electronic stimulation device may be chosen to be driven in a constant voltage mode or a constant current mode. The constant voltage mode is safer than the constant current mode, but the intensity in the constant voltage mode is less stable than in the constant current mode. Choosing which mode depends on the target zone to be electrically stimulated. For example, if the target is dorsal column, the constant current mode is chosen. If the target is the dorsal root ganglion, the constant voltage mode is chosen. When the constant voltage mode is chosen for driving, the voltage of the high-frequency electrical stimulation signal is constant, and the current of the high-frequency electrical stimulation signal varies with the positions and resistances of the first electrode 121 and the second electrode 122. Otherwise, when the constant current mode is chosen for driving, the current of the high-frequency electrical stimulation signal is constant, and the voltage of the high-frequency electrical stimulation signal varies with the positions and resistances of the first electrode 121 and the second electrode 122. For example, in the constant voltage mode, the voltage of the high-frequency electrical stimulation signal ranges from −10V to −1V or from 1V to 10V. Preferably, the voltage of the high-frequency electrical stimulation signal ranges from 10V to −3 V or from 3V to 10V. In the constant current mode, the current of the high-frequency electrical stimulation signal ranges from 2 mA to 50 mA, preferably from 4 ma to 30 mA.

Besides, the frequency of the high-frequency electrical stimulation signal is between 200 KHZ~1000 KHz, preferably between 200 KHz~250 KHz, 250 KHz~350 KHz, 350 KHz~450 KHz, 450 KHz~550 KHz, 550 KHz~650 KHz, 650 KHz~750 KHz, 750 KHz~800 KHz, or 800 KHz~1000 KHz. If the selected frequency is between 200 KHz~450 KHz, the device operates in relatively low frequency so it is less risky to produce biological heat for better safety. Otherwise, if /the selected frequency is between 550 KHz~1000 KHz, the generated electric field has greater density so its electrical stimulation has better performance. In addition, by adjusting the duration time Td, the amount of the electrical stimulation is adjusted and the time for dissipating the produced biological heat accordingly. For example, if the stimulation intensity is relatively low, the duration time Td may be increased to continuously stimulate. If the stimulation intensity and the frequency are relatively high, the duration time Td may be decreased to raise the time for dissipating.

When the electronic stimulation unit 12 receives the high-frequency electrical stimulation signal, the first electrode 121 and the second electrode 122 of the electronic stimulation unit 12 accordingly generate an electric field. The distance from the first electrode 121 and the second electrode 122 to the dorsal root ganglion 3 is arranged within the range of the second interval distance c, so the electric field generated by the first electrode 121 and the second electrode 122 covers the dorsal root ganglion 3. In other words, the electric field covers the dorsal root ganglion 3 and its surroundings to electrically stimulate the target dorsal root ganglion 3 with low intensity, low temperature and high frequency. Without destroying the neural cells of the dorsal root ganglion 3, the biomolecule generation by the dorsal root ganglion 3 is suppressed, and the threshold of the target zone of the dorsal root ganglion 3 is also raised. Thus, the neurotransmission capability of the dorsal root ganglion 3 in the target zone is lowered and the neurotransmission is blocked. As a result, the patient feels nerve pain as little as possible.

Furthermore, the patient may feel as little as possible pain on the target zone without generating relative much sensations of paresthesia if applying the electronic stimulation device for electrical stimulation. The patient suffering pains over a long period of time may accept this electrical stimulation treatment which is effective and generates as little as possible sensations of paresthesia. Preferably, the treatment resulting from the electrical stimulation by the electronic stimulation device in the embodiment may keep effective about one week. In other words, the neurotransmission is blocked about one week. Thus, the patient may less frequently receive the electrical stimulation treatment and it is not necessary for him to receive the treatment frequently so he may be more possibly willing to receive the treatment. Because the details can refer to the later experimental examples, they are not repeated here.

Figure 3A:
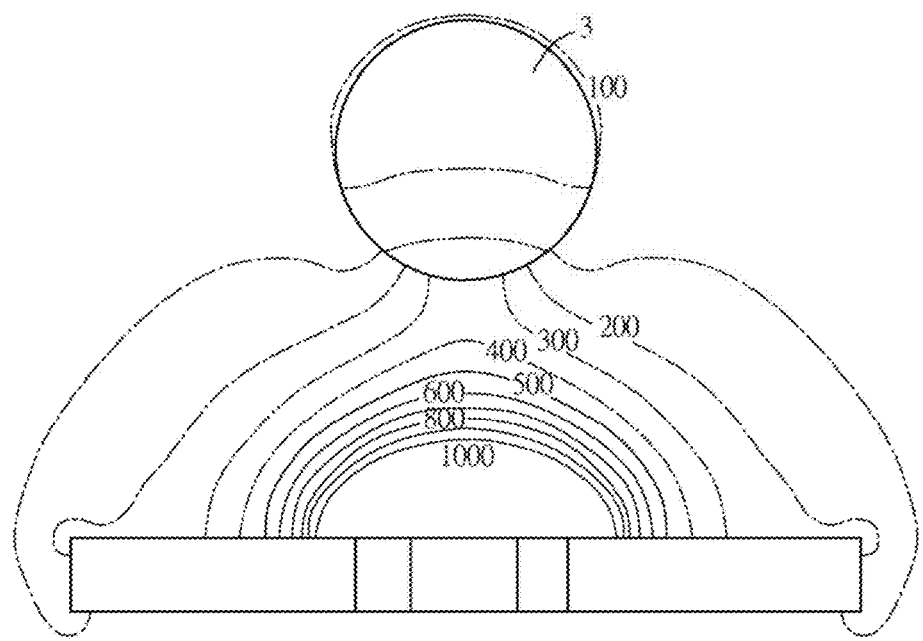
FIG. 3A to 3E and FIG. 4A to 4E are schematic diagrams of the electric field simulation of the electronic stimulation device.
Figure 3B:
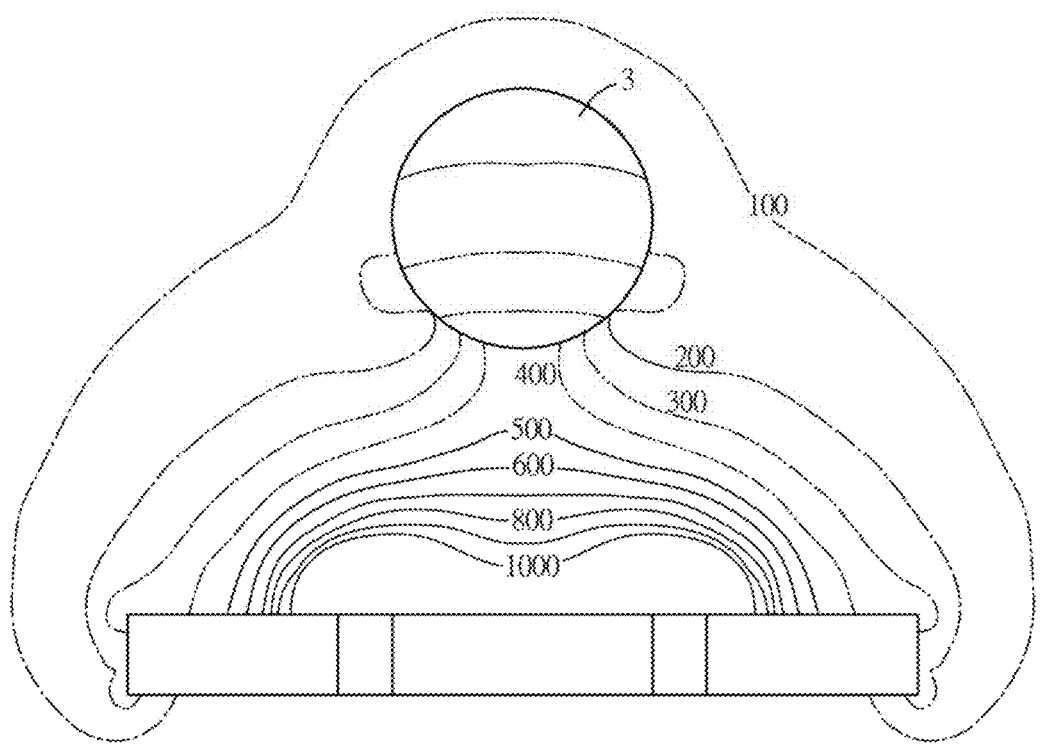
Figure 3C:
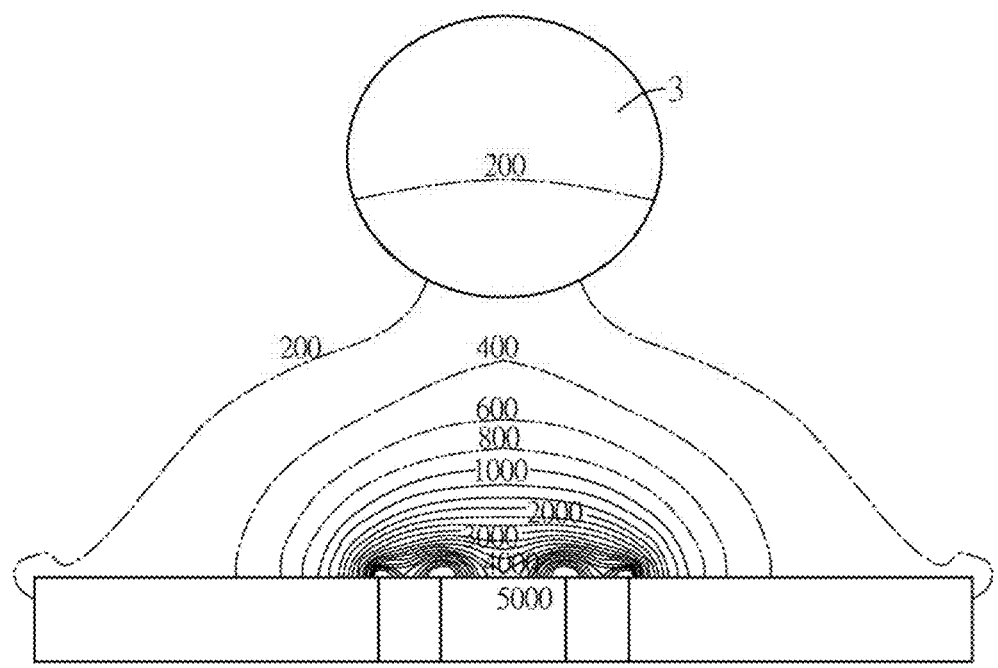
Figure 3D:
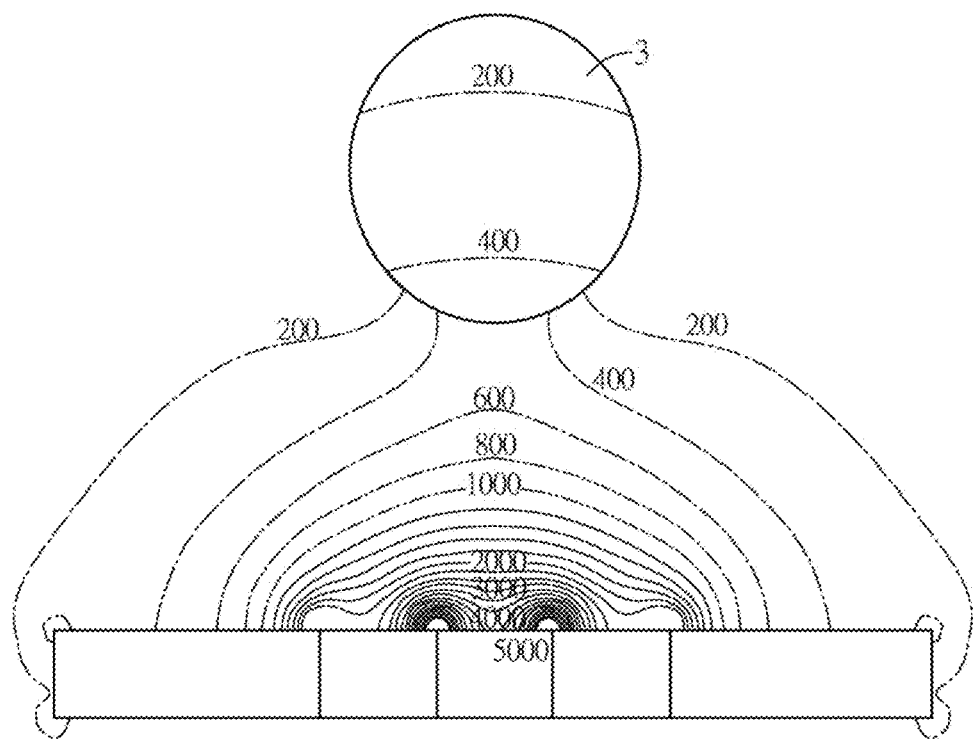
Figure 3E:
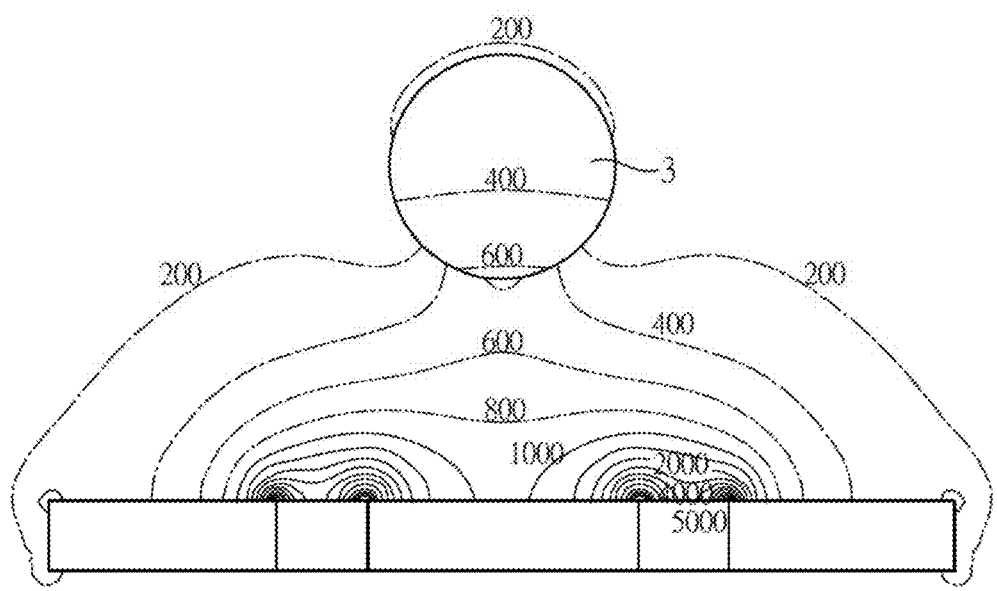

Furthermore, referring to FIG. 3A to FIG. 3D, the field pattern of the electric field is adjusted by adjusting the electrode length a of the first electrode 121 and the second electrode 122, the first interval distance b between the first electrode 121 and the second electrode 122, or the second interval distance c between the first electrode 121, the second electrode 122 and the dorsal root ganglion 3. For example, the voltage of the electrical stimulation signal is 5V, its frequency is 500 KHz, and the distance C is 5 mm. Assuming that the electrode length a and the distance c of the first electrode 121 and the second electrode 122 are constant (a=1 mm, c=5 mm), as smaller the distance b (b=2 mm) between the first electrode 121 and the second electrode 122 as shown in the electric field simulation diagram in FIG. 3, the electric field (the strength of the electric field is 100V/m~1000V/m) may only or mainly effectively cover the dorsal root ganglion 3 to be stimulated; as greater the distance b (b=4 mm) between the first electrode 121 and the second electrode 122 as shown in FIG. 3B, the field pattern of the electric field is distributed expandingly and completely cover the dorsal root ganglion 3 to be stimulated (the drawn strength of the electric field is 100V/m~1000V/m). Relatively, the electric field strength is more intensive if the position is closer to the electromagnetic field of the first electrode 121 and the second electrode 122. As shown in FIG. 3C, it is a distribution diagram of the field pattern that the field pattern of the electric field in FIG. 3A is applied with a more intensive electric field so the strength of the electric field is distributed in the range 100V/m~5000V/m. From the figure, as long as the electrode is disposed close enough to the target zone which is to be stimulated (the distance c is between 0~10 mm), the electric field has an effect on it and the electric field with higher intensity is distributed more closer to the surface of the electrode. Then, referring to FIG. 3D and FIG. 3E, the difference between FIG. 3D and FIG. 3C is the electrode length a of the first electrode 121 and the second electrode 122. In FIG. 3D, the electrode length a is changed to 2 mm. From FIG. 3D, it is seen that the electrode becomes longer and the space distribution of the field pattern of the electric field also becomes slightly larger. The difference between FIG. 3E and FIG. 3D is that the distance b between the electrodes is changed to 6 mm on the condition that the electrode length a of the first electrode 121 and the second electrode 122 are both fixed (at 2 mm) As the distance b between the electrodes is increased, the space distribution of the field pattern of the electric field also becomes larger.

Figure 4A:
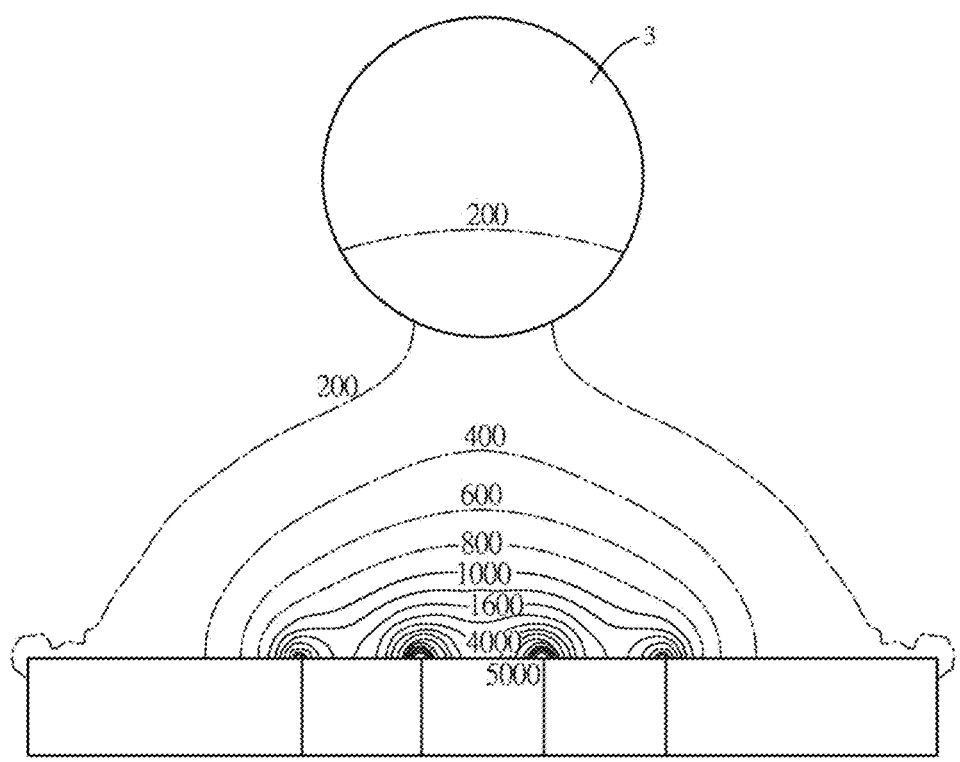
Figure 4B:
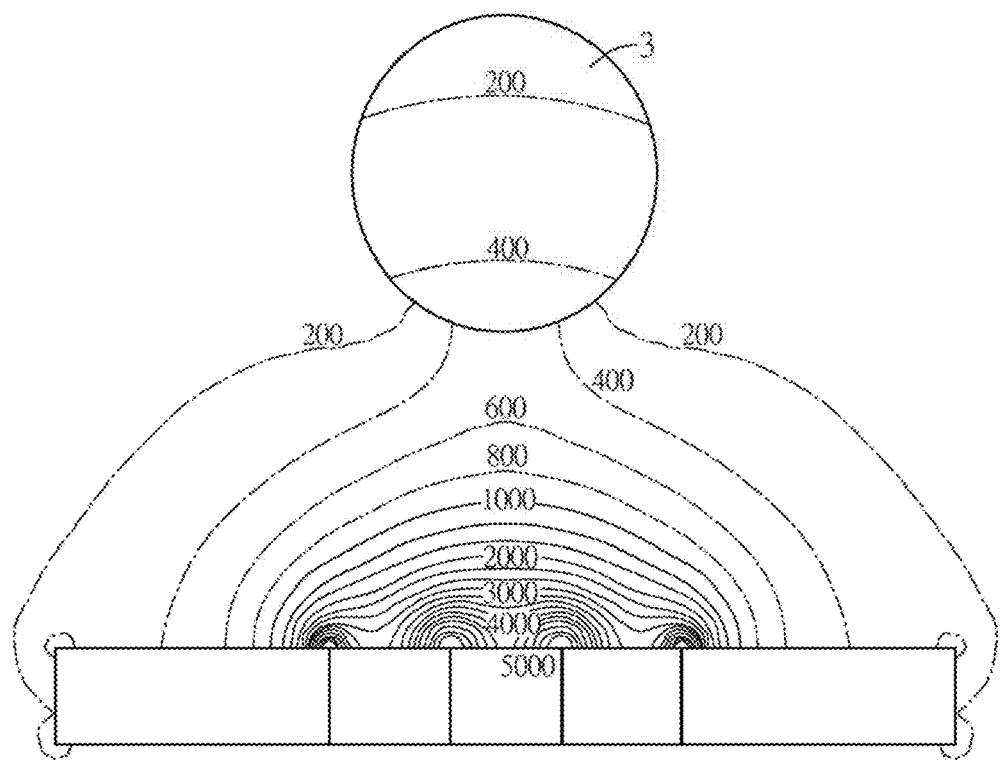
Figure 4C:
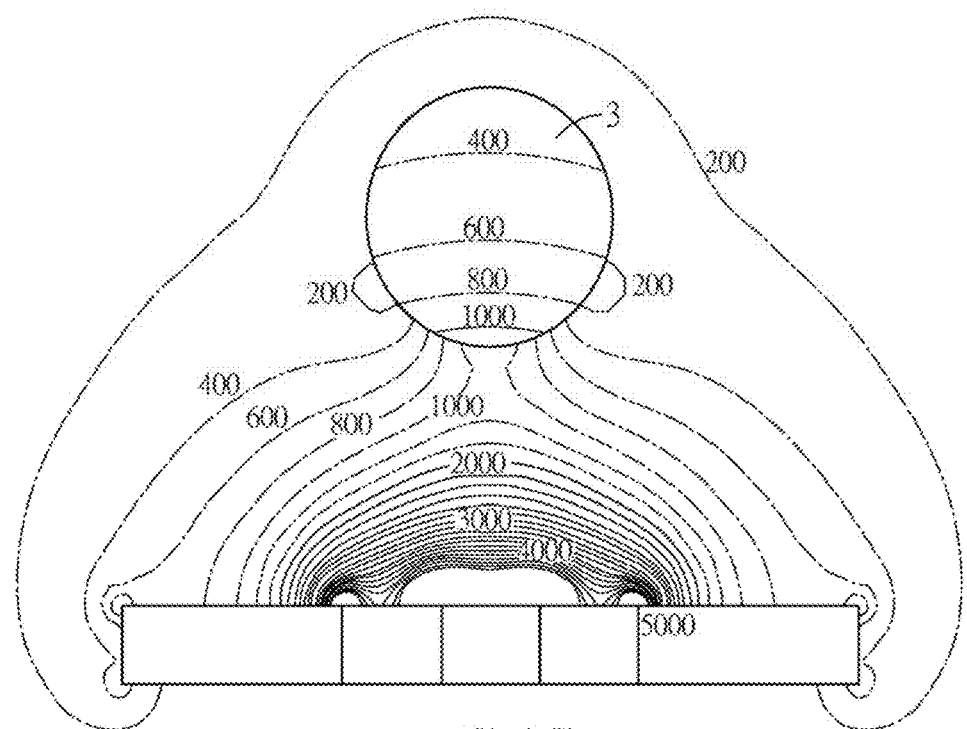

Then, different voltage influences on the space distribution of the field pattern of the electric field are compared. Referring to FIG. 4A to FIG. 4C, the frequency 500 KHz of the constant electrical stimulation signal is applied, and the electrode length a of the first electrode 121 and the second electrode 122, the distance b between the electrodes and the distance c to the target zone to be stimulated are all fixed (a=2 mm, b=2 mm, c=5 mm) Different voltage influences on the space distribution of the field pattern of the electric field are shown in the figures (the voltage is 3V in FIG. 4A, the voltage is 5V in FIG. 4B, the voltage is 10V in FIG. 4C). From the figures, it is seen that as the voltage is greater, the space distribution of the field pattern of the electric field also becomes larger.

Figure 4D:
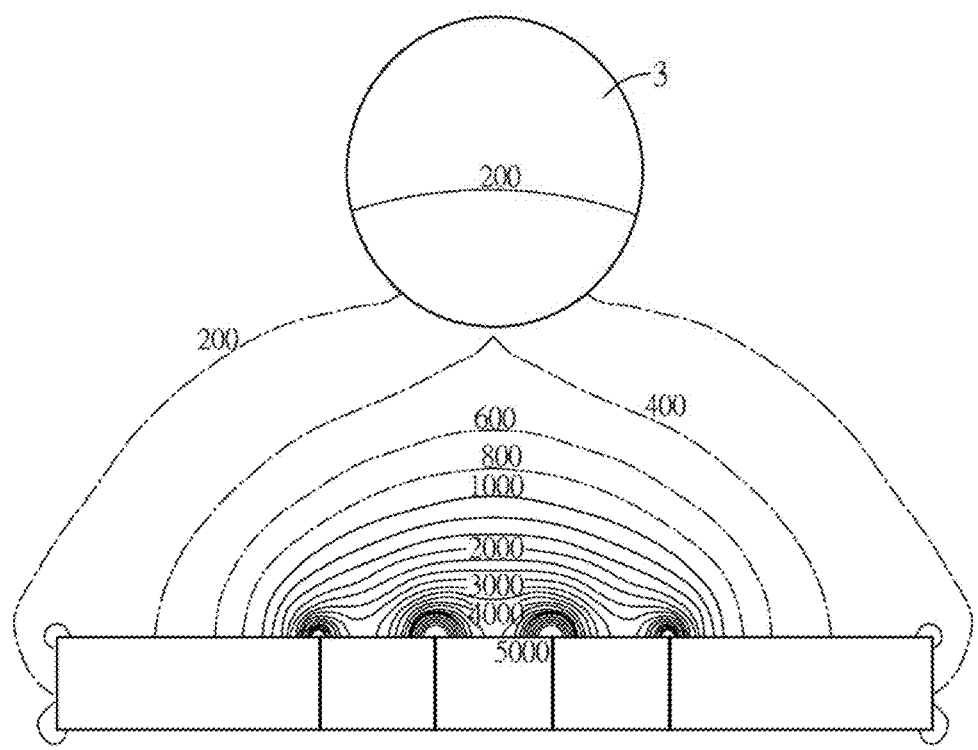
Figure 4E:
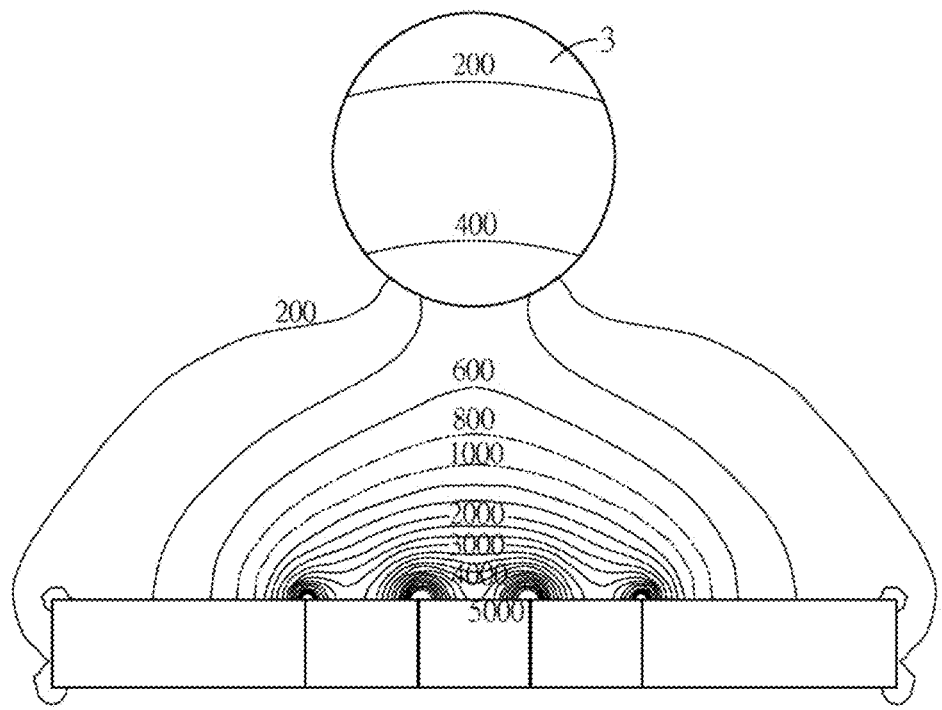

Then, comparing FIG. 4B, FIG. 4D and FIG. 4E, the electrical stimulation signal with 5V is applied, and the electrode length a of the first electrode 121 and the second electrode 122, the distance b between the electrodes, and the distance c to the target zone to be stimulated are all fixed (a=2 mm, b=2 mm, c=5 mm) Different frequency influences of the electrical stimulation signal on the space distribution of the field pattern of the electric field are shown in the figures (the frequency of the electrical stimulation signal is 200 KHz in FIG. 4D, the frequency of the electrical stimulation signal is 500 KHz in FIG. 4B, the frequency of the electrical stimulation signal is 800 KHz in FIG. 4E). From FIG. 5B, because around the arc length at 4 mm it is the point closest to the electronic stimulation unit, the most intensive strength of the electric field is here. As the frequency is increased, the space distribution of the field pattern of the electric field also becomes larger. From FIG. 3A to FIG. 4E, in the embodiment, the electric field strength ranges from 100 V/m to 5000 V/m, preferably from 400 V/m to 5000 V/m.

Figure 5A:
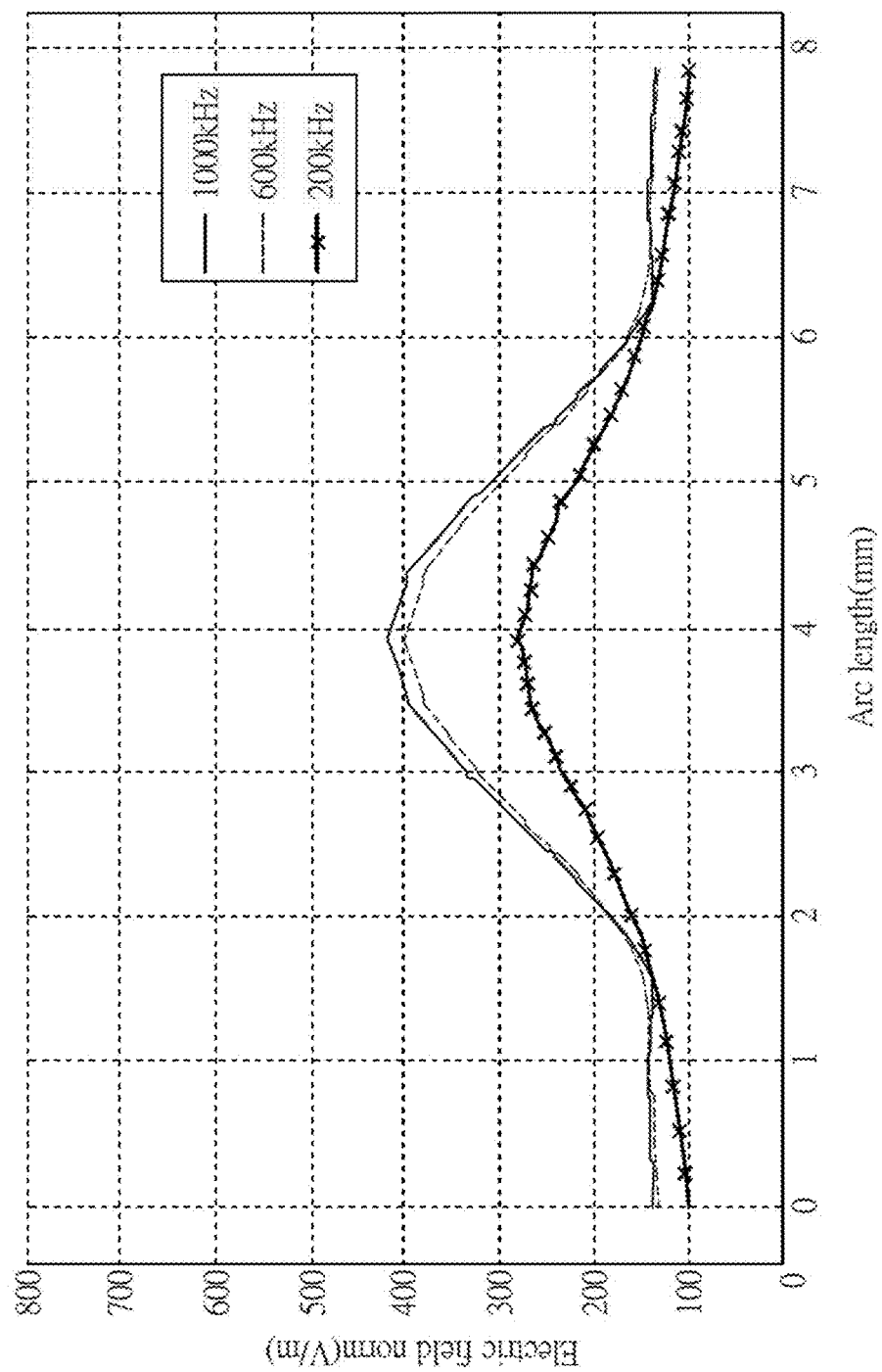

Referring to FIG. 5A and FIG. 5B, the diameter of the target (circular dorsal root ganglion 3) to be stimulated also shown in FIG. 2B is 5 mm, the electrode length a of the first electrode 121 and the second electrode 122 is about 1 mm, the distance c is about 5 mm and the input voltage is 5V. The electric field strength on the target to be stimulated for different arc length location of the electrode (in the horizontal axis, the tangent at the left side of the circle is taken as the start point of the arc 0 mm) is shown in the figures. In FIG. 5A, the corresponding strength of the electric field is detected at different frequencies (200 KHz, 600 KHz and 1000 KHz) for electric stimulation are compared. In FIG. 5B, the corresponding strength of the electric field is detected at different distances b between electrodes (b is 2, 3, 4, 5, or 6 mm.) From FIG. 5A, as the frequency of the electric stimulation signal is increased, the strength of the electric field is more intensive and the space distribution of the field pattern of the electric field also becomes larger. For example, under the condition that the frequency of the electric stimulation signal is 1000 KHz, the maximum strength of the electric field at the target zone may reach 400 V/m. Under the condition that the frequency of the electric stimulation signal is 200 KHz, the maximum strength of the electric field at the target zone may be not intensive enough to reach 300 V/m. From FIG. 5B, if the distance b is between 4 mm~6 mm, the electric field strength of the electromagnetic field reaches its maximum.

After the electronic stimulation unit 12 is implanted in the organism, to utilize it as fully as possible, the electronic stimulation device 1 of the embodiment is able to operate in a low-frequency mode to assist the doctor in checking whether the electrodes are at correct positions after the implantation. For example, in the low-frequency mode, the electronic stimulation unit 12 may deliver a low-frequency electrical stimulation signal of which the frequency is between 0.1 Hz~1 KHz and its pulse width is between 10 µs~500 µs. The electronic stimulation unit 12 delivers the low-frequency electrical stimulation signal to detect the corresponding spasm of the muscle so as to check whether the implanted electronic stimulation unit is loose or at wrong positions.

Figure 6:
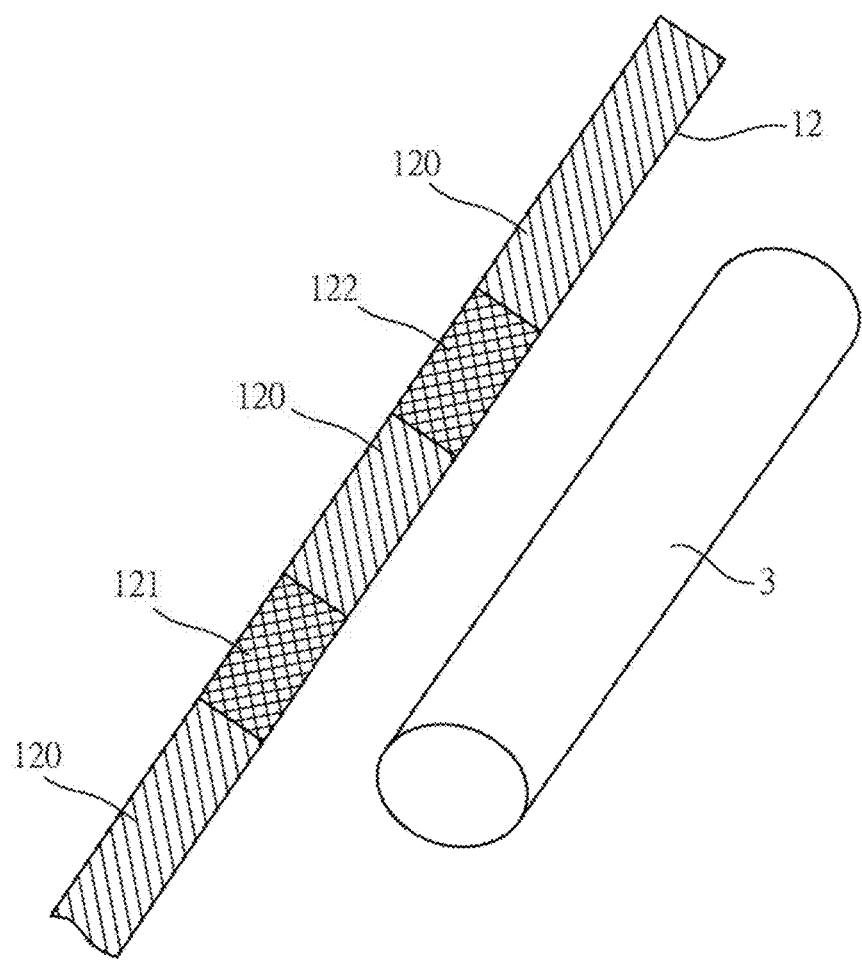
FIG. 6 is another schematic diagram showing the electronic stimulation device in FIG. 1A.

Referring to FIG. 2A and FIG. 6, in the embodiment, the electronic stimulation unit 12 is like a straight line, but it is not limited thereto. The shape of the electronic stimulation unit 12 may be like the shape described in the following embodiments, but it is not limited thereto.

In the embodiment, the electronic stimulation device 1 is an active electronic stimulation device of which the first control unit 11 together with the electronic stimulation unit 12 are implanted in the target zone of the organism. In other words, both the first control unit 11 and the electronic stimulation unit 12 are implanted in the organism subcutaneously. Alternatively, the first control unit 11 and the electronic stimulation unit 12 are integrated into one part first and then implanted subcutaneously. Because of electrically coupled to the controller 2 outside the organism, the first control unit 11 can receive the parameter signal and energy from the second control unit 21 so the electronic stimulation unit 12 may electrically stimulate the target zone of the organism.

Figure 7:
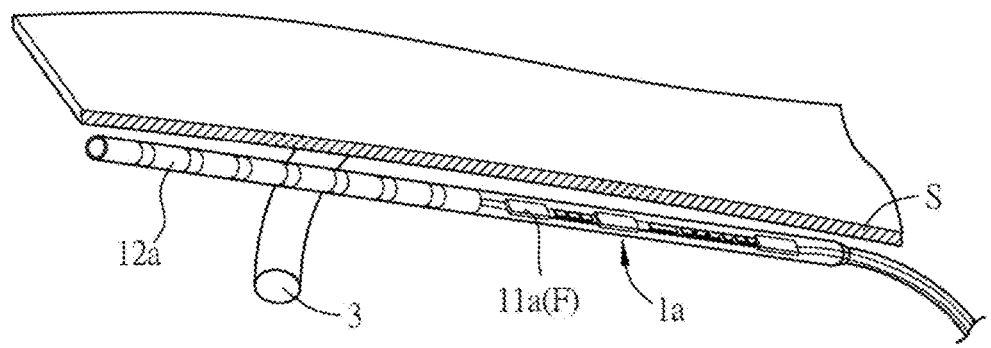
FIG. 7 to FIG. 8 are schematic diagrams showing another examples of the electronic stimulation device according to other embodiments.

The electronic stimulation device of the disclosure is not limited to the electronic stimulation device 1 mentioned above. In other embodiment, the active electronic stimulation device may be like the electronic stimulation device in FIG. 7. The electronic stimulation device 1a in the embodiment and the electronic stimulation device 1 in the previous embodiment have substantially alike elements thereof, and the first control unit 11a and the electronic stimulation unit 12a are also respectively implanted in the epidermis S of the organism (subcutaneous). However in the embodiment, the first control unit 11a of the electronic stimulation device 1a is a FPCB (flexible printed circuit board) integrated in the electronic stimulation unit, and it still can receive the parameter signal and electrical energy from the second control unit (not shown in the figure) outside the organism, and deliver the electrical stimulation signal to the electronic stimulation unit 12a to electrically stimulate the dorsal root ganglion 3 of the organism. In the embodiment, the electronic stimulation device 1a may be narrowed enough to be implanted subcutaneously for abating the burden of the organism (or the patient).

Figure 8:
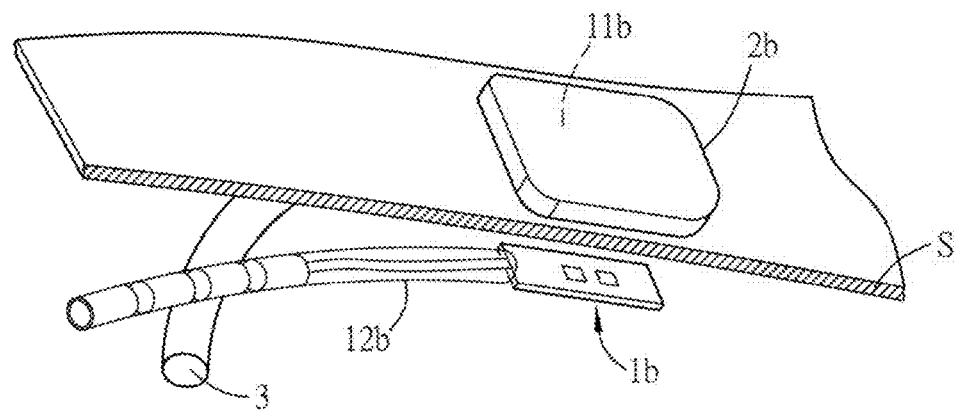

Alternatively, the electronic stimulation device may be like the device shown in FIG. 8. Referring to FIG. 8, in the embodiment, the electronic stimulation device 1b is a passive electronic stimulation device. However, the first control unit 11b of the electronic stimulation device 1b is integrated in the controller 2 outside the epidermis S of the organism (subcutaneous). Thus, the implanted electronic stimulation device 1b does not contain the control unit therein. The electronic stimulation unit 11b (lead) at its end has a FPCB which is implanted subcutaneously and not deeply (for example the depth is less than 5 cm). The controller 2b which is not implanted within the skin can deliver an electrical stimulation signal to the electronic stimulation unit 11b, so the electronic stimulation unit 12b can electrically stimulate the dorsal root ganglion 3 of the organism.

Figure 9:
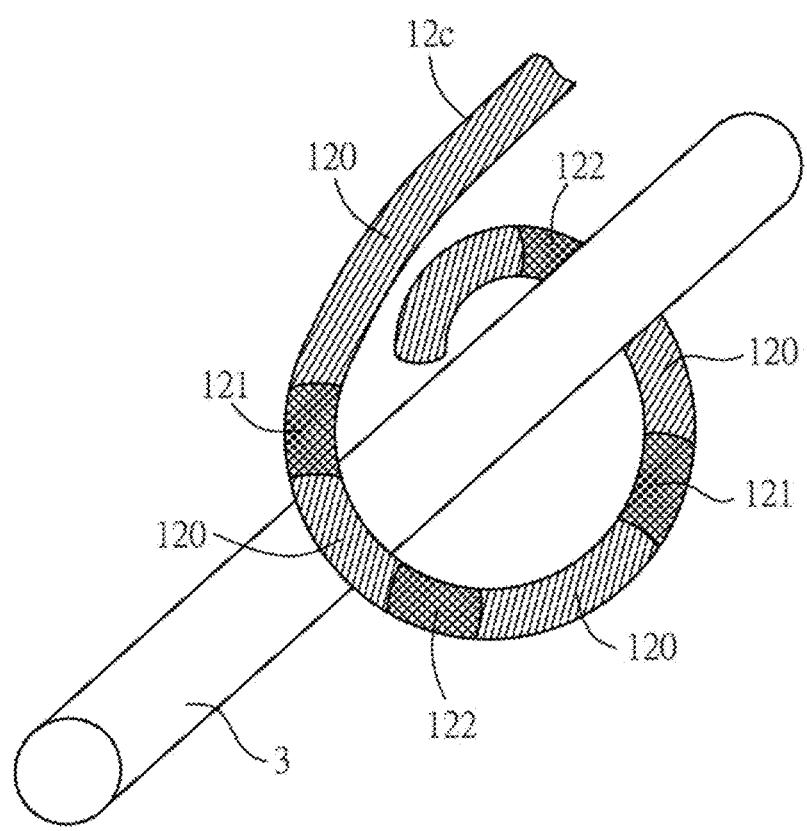
FIG. 9 to FIG. 14 are schematic diagrams showing another examples of the electronic stimulation device.
Figure 12:
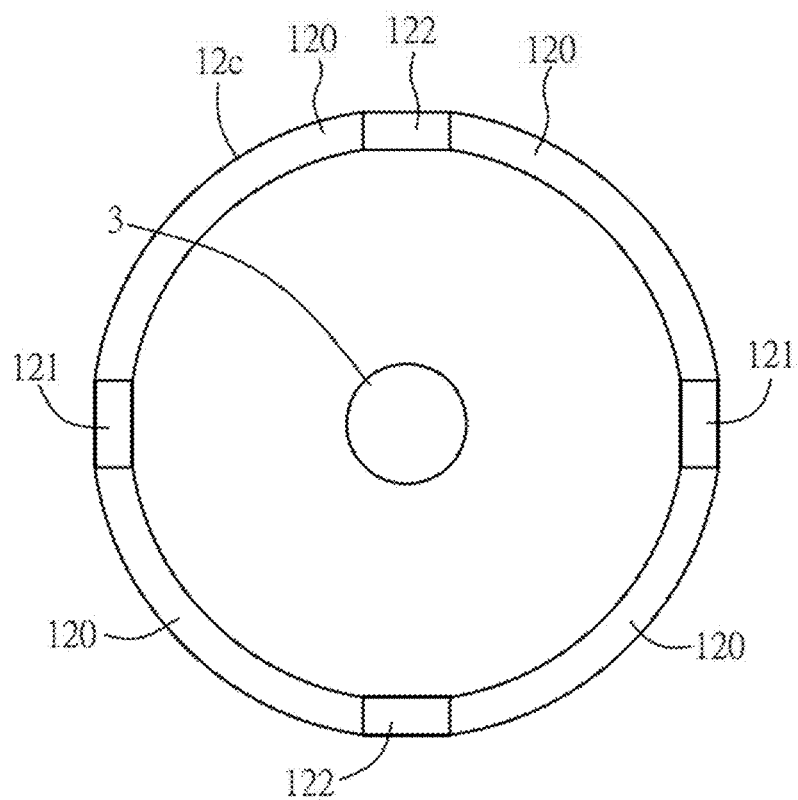
Figure 13:
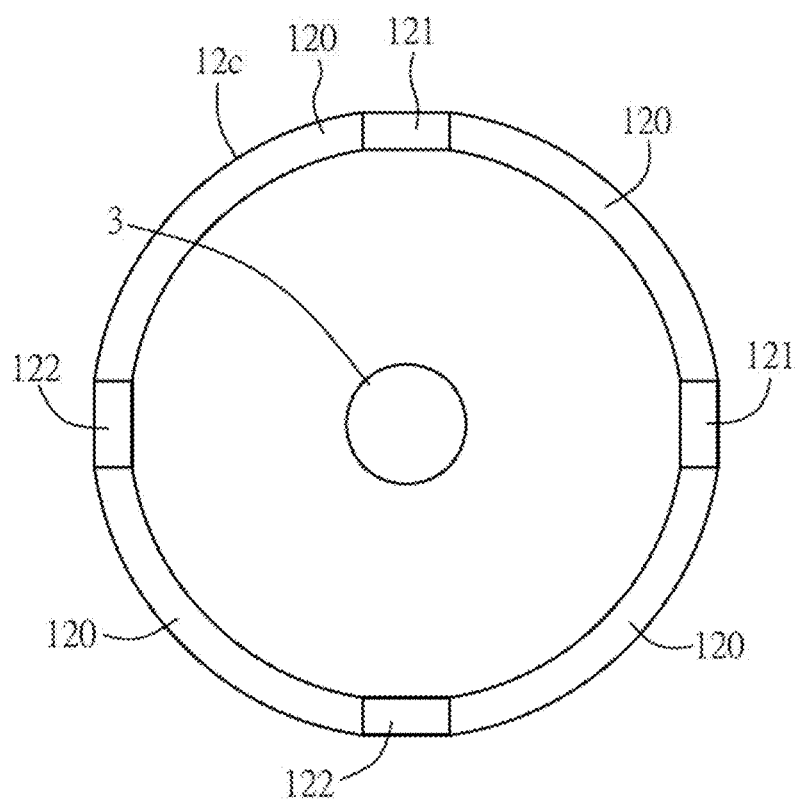
Figure 14:
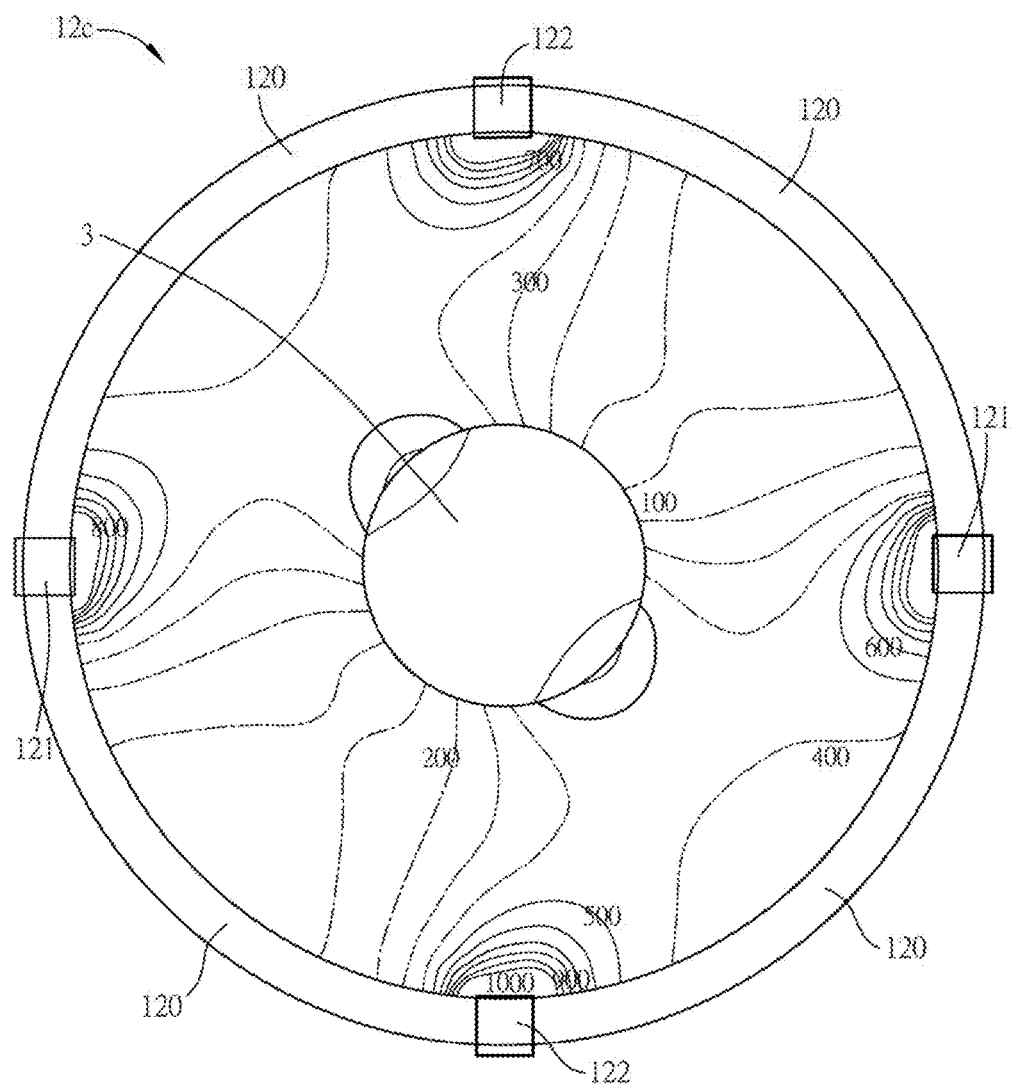

As to implementation of the electronic stimulation unit, it is not limited to the above electronic stimulation unit 12. FIGS. 9, 12, 13 illustrate another embodiment. In the embodiment, the electronic stimulation unit 12c is like a ring, and the electronic stimulation unit 12c includes at least two first electrodes 121 and at least two second electrodes 122. The first electrodes 121 and the second electrode 122 are interlaced at intervals (as shown in FIG. 12). Alternatively, the first electrodes 121 and the second electrodes 122 may be arranged sequentially without interlacement (as shown in FIG. 13). The electric field generated by the first electrode 121 and the second electrode 122 of the electronic stimulation unit 12 surrounds and covers the target dorsal root ganglion 3 (as shown in FIG. 14) to stimulate it with low intensity, low temperature and high frequency electromagnetism. Furthermore, if the position is closer to the first electrode 121 and the second electrode 122, the electric field is more intensive.

Figure 10:
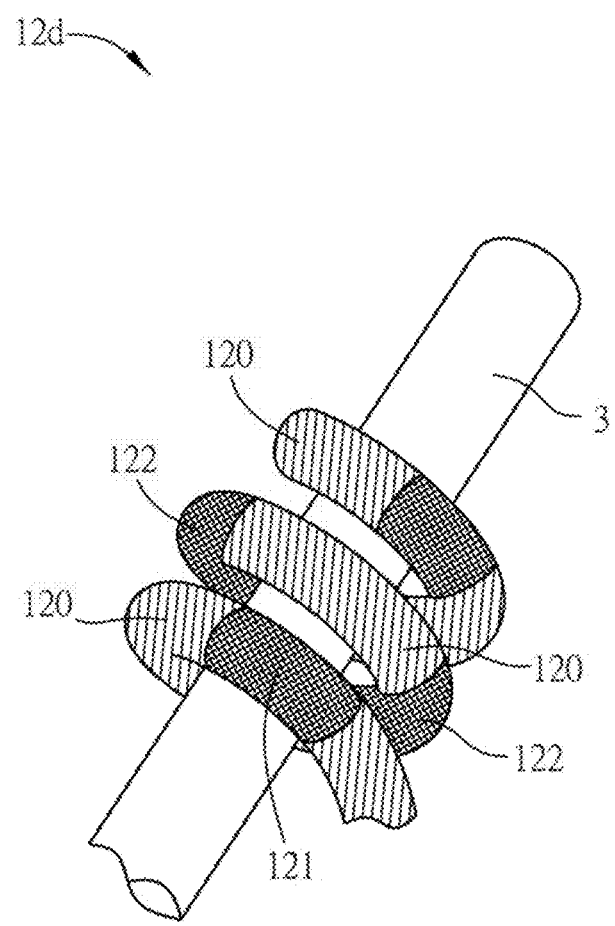

Referring to FIG. 10, the electronic stimulation unit 12d may be like a helix, and the electronic stimulation unit 12d includes at least two first electrodes 121 and at least two second electrodes 122. In the embodiment, the electronic stimulation unit 12d includes two first electrodes 121 and two second electrodes 122 for example. The arrangement of the first electrode 121 and the second electrode 122 is not limited. The first electrodes 121 and the second electrodes 122 may be interlaced or arranged without interlacement, and the first electrodes 121 and the second electrodes 122 may be arranged like a helix to surround the dorsal root ganglion 3. Because the electric field generated by the first electrodes 121 and the second electrodes 122 like a helix surround and cover the target dorsal root ganglion 3, the target dorsal root ganglion 3 is electrically stimulated with low intensity, low temperature and high frequency.

Figure 11:
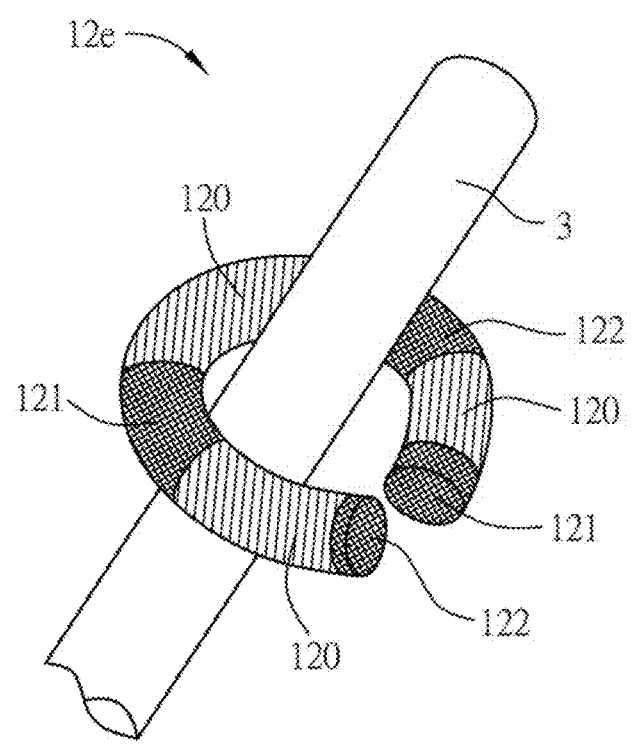

Referring to FIG. 11, in the embodiment, the electronic stimulation unit 12e is like an arc, and the electronic stimulation unit 12e includes at least two first electrodes 121 and at least two second electrodes 122. In the embodiment, the electronic stimulation unit 12e includes two first electrodes 121 and two second electrodes 122 for example. The arrangement of the first electrodes 121 and the second electrodes 122 is not limited. The first electrodes 121 and the second electrodes 122 may be interlaced or arranged without interlacement, and the first electrodes 121 and the second electrodes 122 may be arranged to surround the dorsal root ganglion 3. Because the electric field generated by the first electrode 121 and the second electrode 122 surround and cover the dorsal root ganglion 3, the target dorsal root ganglion 3 is stimulated with low intensity, low temperature and high frequency.

Figure 15:
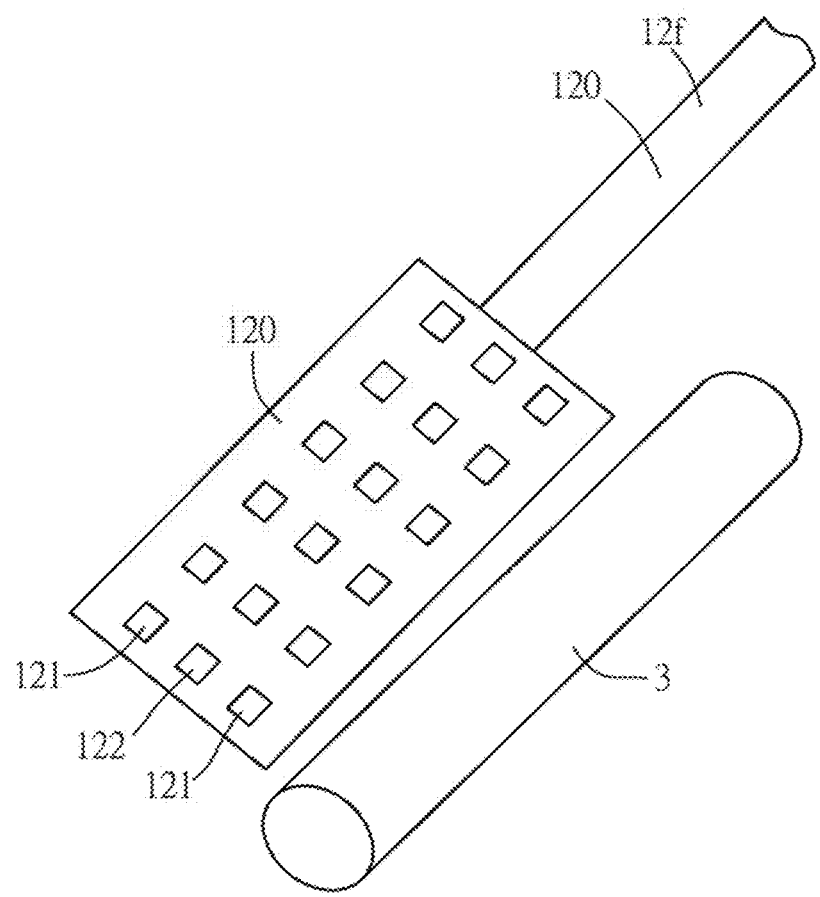
FIG. 15 is a schematic diagrams showing the application of high stimulation device according to an embodiment.

Referring to FIG. 15, in the embodiment, the electronic stimulation unit 12f is like a flake (or a flat), and the electronic stimulation unit 12f includes a plurality of the first electrodes 121 and a plurality of the second electrodes 122. These first electrodes 121 and these second electrodes 122 are arranged at intervals in an array. Similarly, the electric field generated by the first electrode 121 and the second electrode 122 surrounds and covers the dorsal root ganglion 3 so as to electrically stimulate the target, the dorsal root ganglion 3, with low intensity and low temperature.

From the below experiments, the operation and effect of the electronic stimulation device which stimulates the dorsal root ganglion are explained. However, the below examples are just explanatory but not limited to the scope of the invention.

EXPERIMENTAL EXAMPLE 1

The Pain Behavior Test on the Foot in the Rat—Von Frey (VF) Test

Sprague-Dawley rats (SD rats) of about 275-350 grams weight are used (BioLASCO, Taiwan co., Ltd., Taiwan) and they are provided from the central laboratory animal center of Shin Kong Wu Ho-Su Memorial Hospital. The spinal nerve ligation (SNL) is performed on the L5 spinal nerve of the SD rat. After the development of the pain behavior is stable for few days and conforms to the clinical pain development model, the electronic stimulation unit 1 is implanted and then the high-frequency electrical stimulation therapy is performed. In this experimental example, the rats are divided into the control group (N=3) and the experimental group (N=7) according to the different electrical stimulation treatments. As to the experimental group, the pain behavior is continuously observed for 7 days after surgery. After the pain behavior is stable, the high-frequency electrical stimulation therapy is performed for 5 minutes once a week totally three times, and the responses to the pain behavior tests are observed. The results are shown in FIG. 16.

Figure 16:
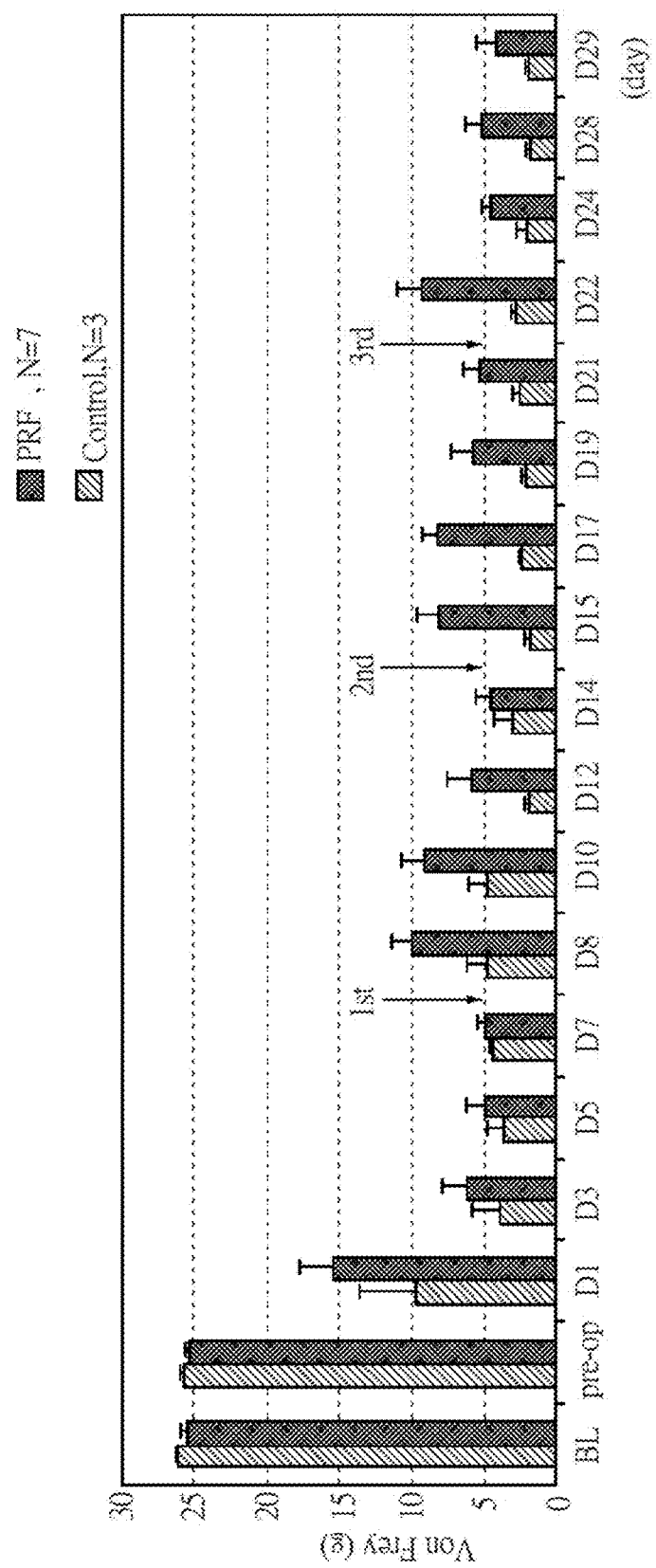
FIG. 16 showing the result of the pain behavior test on the foot in the rat—Von Frey (VF)

As shown in FIG. 16, the pain behavior of the control group becomes stable on the third day until the 29th day, and Von Frey pain pressure thresholds are all less than 5 g (between 1.72±0.39 g and 4.85±1.31 g). As to the experimental group, its pain behavior is similar to that of the control group before receiving high-frequency electrical stimulation therapy (on the 7th day, D7) and becomes stable on about the third day similarly. However, after receiving the first (D7) high-frequency electrical stimulation, its Von Frey pain pressure thresholds are improved. They are different from the control group (D8: 4.73±1.47 g; D10: 4.85±1.31 g) both on D8 (9.85±1.56 g) and D10 (9.0±1.68 g), the tolerance levels of the pressure thresholds in the experimental group are improved up to about 10 g, the pain pressure thresholds increase to about 2.08 times as compared with the control group, and the pain relief will gradually decay until receiving the second high-frequency electrical stimulation therapy (the experimental group D14: 4.53±1.08 g; the control group D14: 2.98±1.44 g). On the next day after receiving the second (D14) high-frequency electrical stimulation therapy (the experimental group D15: 8.12±1.65 g; the control group D15: 1.81±0.53 g; the pain pressure threshold of the experimental group is about 4.49 times greater than that of the control group), the therapy of receiving the first high-frequency electrical stimulation is still effective. The response to the pain behavior test is still excellent on the next day after receiving the third (D21) high-frequency electrical stimulation therapy (the experimental group D22: 9.17±1.93 g; the control group D22: 2.73±0.57 g; the pain pressure threshold of the experimental group is about 3.36 times greater than that of the control group). Obviously, the pain can be immediately relieved, and there are differences of the pain pressure thresholds between the experimental group and the control group every time after receiving the high-frequency electrical stimulation therapy. It approves that after the electrical stimulation unit of the invention is implanted, receiving the high-frequency electrical stimulation therapy for 5 minutes once a week can relieve the pain for a short time.

EXPERIMENTAL EXAMPLE 2

Neuroelectrophysiological Test

SD rats are divided into the experimental group and the control group, the experimental group (FIG. 17B) receives the high-frequency electrical stimulation for 5 minutes, and the control group (FIG. 17A) does not receive any electrical stimulation. The two groups receive large current stimulation (2.5T, C response threshold) on the sciatic nerve under the same conditions so as to induce obvious A responses (referring to A-fiber) and C responses (referring to C-fiber) occurring in the ipsilateral spinal dorsal horn. Before the interventional measure (high-frequency electrical stimulation for 5 minutes or suspending recording for 5 minutes), the baseline is measured for 30 minutes (18 samples, 100 seconds interval) in advance. After the interventional measure is provided, the large current stimulation is performed on the sciatic nerve once every 30 minutes, the data are continuously recorded for 2 hours, and 5 experimental waveforms are respectively generated in two groups. The results of the control group and the experimental group are respectively shown in FIG. 17A and FIG. 17B.

Figure 17A:
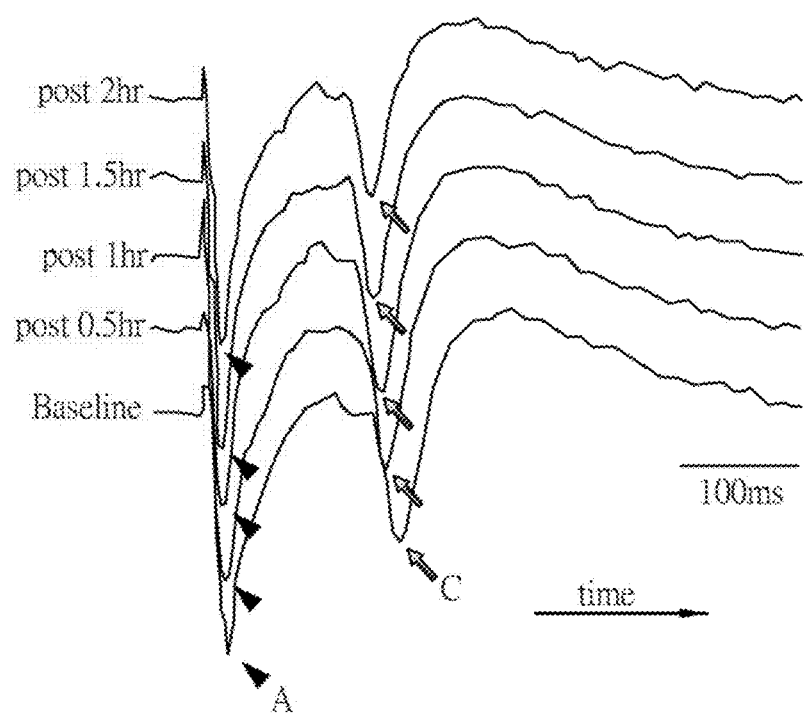
FIG. 17A and FIG. 17B respectively showing the results of the control group and the experimental group of neuro-electrophysiological test.
Figure 17B:
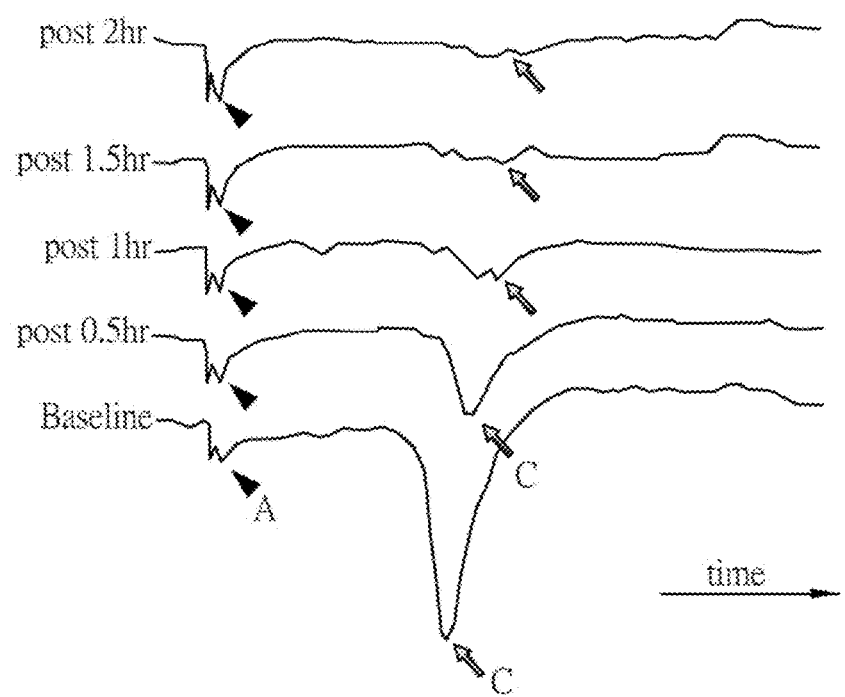

In this experiment, as to the rats receiving the high-frequency electrical stimulation for 5 minutes, the mean values of the neural responses for every 30 minutes are aligned at the point of 90 ms first, and then the individual time of each group are compared. Referring to FIG. 17A and FIG. 17B, the mean lines of interval of every 30 minutes are put together for comparison. Here, there are no significant differences between the curves of individual time in the control group shown in FIG. 17A. Compared with the control group, it can be seen from FIG. 17B that the C-component is relatively largely reduced after the high-frequency electrical stimulation in comparison with the baseline in the experimental group.

In detail, the large current stimulation on the peripheral sciatic nerve acts as the source of pain in this experimental example, and the signal can be transmitted to the dorsal root ganglion and the spinal dorsal root nerves through A-fibers and C-fibers by nerve conduction. The neural response to the interventional measure of high-frequency electrical stimulation can be observed by electrophysiological measurement of nerve conduction. From FIG. 17B, the induced C response is relatively largely reduced with time after receiving the high-frequency electrical stimulation, and the area of the C-component (intensity) is also reduced with time. It shows that the axon of the C-fiber which is responsible for sense of pain (especially the pain which is chronic and difficult to locate) is changed in transmission. The high-frequency electrical stimulation blocks or inhibits the signal transmission of neuron in some fibers, so the pain can be relieved, even totally blocked.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. An electronic stimulation device for electrically stimulating a target zone of an organism for pain management, comprising:

at least one electronic stimulation unit including at least one first electrode and at least one second electrode, wherein the electronic stimulation unit is configured to be implanted in the organism and delivers an electrical stimulation signal to impel the first electrode and the second electrode to generate an electric field, the frequency of the electrical stimulation signal ranges from 200 KHz to 1000 KHz, the range of the electric field covers the target zone, and the electric field strength is larger than 100V/m and smaller than 1000V/m for electrically stimulating the target zone without destroying the neural cells of the target zone and without nerve blocking agent, wherein the electronic stimulation unit delivers the electrical stimulation signal for a second time from 2 hours to 7 days after the electronic stimulation unit delivers the electrical stimulation signal for a first time, so as to electrically stimulate the target zone again.

2. The electronic stimulation device according to claim 1, wherein the electrical stimulation signal is a pulse signal, and the pulse signal is a sine wave, a triangle wave, or a square wave.

3. The electronic stimulation device according to claim 1, wherein the voltage of the electrical stimulation signal ranges from −10V to −1V or ranges from 1V to 10V.

4. The electronic stimulation device according to claim 1, wherein the current of the electrical stimulation signal ranges from 2mA to 50mA.

5. The electronic stimulation device according to claim 1, wherein the distance from the first electrode to the second electrode ranges from 1mm to 7mm, and the distance between the first electrode, the second electrode and the target zone ranges from 0 to 10mm.

6. The electronic stimulation device according to claim 1, wherein the electrical stimulation signal is adapted to block the neurotransmission in the target zone through a c-fiber.

7. The electronic stimulation device according to claim 1, wherein the target zone is brain, vertebral column, dorsal root ganglion and/or spinal dorsal horn.

8. The electronic stimulation device according to claim 1, wherein the frequency of the electrical stimulation signal is less than 1 KHz.

9. A method of treatment applied to electrically stimulate a target zone of an organism by a stimulation device for pain management, wherein the stimulation device includes an electronic stimulation unit, comprising:
  implanting the electronic stimulation unit including at least one first electrode and at least one second electrode in the organism and placing the electronic stimulation unit near the target zone;
  delivering an electrical stimulation signal by the electronic stimulation unit, wherein the frequency of the electrical stimulation signal ranges from 200 KHz to 1000 KHz;
  generating an electric field covering the target zone by the first electrode and the second electrode, wherein the electric field strength is larger than 100V/m and smaller than 1000V/m;
  electrically stimulating the target zone without destroying the neural cells of the target zone and without nerve blocking agent; and
  delivering the electrical stimulation signal for a second time from 2 hours to 7 days after the electronic stimulation unit delivers the electrical stimulation signal for a first time, so as to electrically stimulate the target zone again.

10. The method according to claim 9, wherein the electrical stimulation signal is a pulse signal, and the pulse signal is a sine wave, a triangle wave, or a square wave.

11. The method according to claim 9, wherein the voltage of the electrical stimulation signal ranges from −10V to −1V or ranges from 1V to 10V.

12. The method according to claim 9, wherein the current of the electrical stimulation signal ranges from 2mA to 50mA.

13. The method according to claim 9, wherein the electrical stimulation signal is used by the electronic stimulation device to block the neurotransmission in the target zone through a c-fiber.

14. The method according to claim 9, wherein the target zone is brain, vertebral column, dorsal root ganglion and/or spinal dorsal horn.

15. An electronic stimulation system, comprising:
  a control unit; and
  an electronic stimulation device comprising at least one electronic stimulation unit configured to be implanted in the organism and including at least one first electrode and at least one second electrode, wherein the controller directs the electronic stimulation unit to deliver an electrical stimulation signal to impel the first electrode and the second electrode to generate an electric field, the frequency of the electrical stimulation signal ranges from 200 KHz to 1000 KHz, the range of the electric field covers a target zone and the electric field strength is larger than 100V/m and smaller than 1000V/m for electrically stimulating the target zone without destroying the neural cells of the target zone and without nerve blocking agent,
  wherein the electronic stimulation unit delivers the electrical stimulation signal for a second time from 2 hours to 7 days after the electronic stimulation unit delivers the electrical stimulation signal for a first time, so as to electrically stimulate the target zone again.

16. The electronic stimulation system according to claim 15, wherein the voltage of the electrical stimulation signal ranges from −10V to −1V or ranges from 1V to 10V.

17. The electronic stimulation system according to claim 15, wherein the current of the electrical stimulation signal ranges from 2mA to 50mA.

18. The electronic stimulation system according to claim 15, wherein the electrical stimulation signal is a pulse signal, and the pulse signal is a sine wave, a triangle wave, or a square wave.

19. The electronic stimulation system according to claim 15, wherein the electrical stimulation signal is adapted to block the neurotransmission in the target zone through a c-fiber.

20. An electronic stimulation device for electrically stimulating a target zone of an organism, comprising:
  at least one electronic stimulation unit including at least one first electrode and at least one second electrode, wherein the electronic stimulation unit is configured to be implanted in the organism and delivers an electrical stimulation signal to impel the first electrode and the second electrode to generate an electric field, the range of the electric field covers the target zone, and the electric field strength is larger than 100V/m and smaller than 1000V/m for electrically stimulating the target zone without destroying the neural cells of the target zone and without nerve blocking agent,
  wherein the electronic stimulation unit delivers the electrical stimulation signal for a second time from 2 hours to 7 days after the electronic stimulation unit delivers the electrical stimulation signal for a first time, so as to electrically stimulate the target zone again.

21. The electronic stimulation device according to claim 20, wherein the frequency of the electrical stimulation signal ranges from 200 KHz to 1000 KHz.

22. A method of treatment applied to electrically stimulate a target zone of an organism by a stimulation device, wherein the stimulation device includes an electronic stimulation unit, comprising:

implanting the electronic stimulation unit including at least one first electrode and at least one second electrode in the organism and placing the electronic stimulation unit near the target zone;

delivering an electrical stimulation signal by the electronic stimulation unit;

generating an electric field covering the target zone by the first electrode and the second electrode, wherein the electric field strength is larger than 100V/m and smaller than 1000V/m;

electrically stimulating the target zone without destroying the neural cells of the target zone and without nerve blocking agent; and delivering the electrical stimulation signal for a second time from 2 hours to 7 days after the electronic stimulation unit delivers the electrical stimulation signal for a first time, so as to electrically stimulate the target zone again.

23. The method of treatment according to claim 22, wherein the frequency of the electrical stimulation signal ranges from 200 KHz to 1000 KHz.

\* \* \* \* \*